United States Patent [19]

Peter et al.

[11] 4,269,977

[45] May 26, 1981

[54] PROCESS FOR THE MANUFACTURE OF 8-OXO-5-THIA-1-AZABICYCLO [4,2,0]OCT-2-ENE OR 3-ENE COMPOUNDS

[75] Inventors: Heinrich Peter, Riehen; Hans Bickel, Binningen, both of Switzerland

[73] Assignee: Ciba-Geigy Corporation, Ardsley, N.Y.

[21] Appl. No.: 670,035

[22] Filed: Mar. 24, 1976

Related U.S. Application Data

[63] Continuation of Ser. No. 255,826, May 22, 1972, abandoned.

[30] Foreign Application Priority Data

May 24, 1971 [CH] Switzerland .................... 7540/71
Apr. 13, 1972 [CH] Switzerland .................... 5425/72

[51] Int. Cl.$^2$ ........................................... C07D 501/04
[52] U.S. Cl. .................................... 544/16; 544/22; 544/23; 424/246
[58] Field of Search ............... 260/243 C; 544/23, 16, 544/22

[56] References Cited

U.S. PATENT DOCUMENTS

| 3,351,596 | 11/1967 | Chamberlin | 260/243 C |
| 3,532,694 | 10/1970 | Somerfield | 260/243 C |
| 3,932,393 | 1/1976 | Chavvette | 260/243 C |

OTHER PUBLICATIONS

Urry et al., J. Org. Chem. vol. 29, 1663 (1964).
Nilt et al., J. Org. Chem. vol. 33, 923 (1968).

*Primary Examiner*—Nicholas S. Rizzo
*Attorney, Agent, or Firm*—Prabodh I. Almaula

[57] ABSTRACT

The invention concerns the decarbonylation of the formyl group in 7-amino-3-formyl-ceph-2-em-4-carboxylic acid compounds and 7-amino-3-formyl-ceph-3-em-4-carboxylic acid compounds by treatment with a platinum metal complex capable of taking up carbon monoxide. Also included are the 7-amino-ceph-2-em-4-carboxylic acid compounds and the 1-oxides of 7-amino-ceph-3-em-4-carboxylic acid compounds; these compounds are used as intermediates.

7 Claims, No Drawings

PROCESS FOR THE MANUFACTURE OF 8-OXO-5-THIA-1-AZABICYCLO [4,2,0]OCT-2-ENE OR 3-ENE COMPOUNDS

This is a continuation of application Ser. No. 255,826, filed May 22, 1972, now abandoned.

The subject of the present invention is a process for the manufacture of 7-amino-8-oxo-5-thia-1-azabicyclo [4,2,0]-oct-2-ene-2-carboxylic acid compounds or -3-ene-2-carboxylic acid compounds, especially 7β-amino-cephem-4-carboxylic acid compounds of the formula

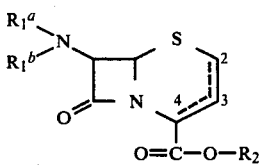

wherein $R_1{}^a$ represents hydrogen or an amino protective group $R_1{}^A$ and $R_1{}^b$ represents hydrogen or an acyl group Ac, or $R_1{}^A$ and $R_1{}^b$ together represent a bivalent amino protective group, and $R_2$ represents hydrogen or an organic radical $R_2{}^A$ which together with the —C(=O)—O— grouping forms a protected carboxyl group, and which contain a double bond in the 2,3- or 3,4-position, as well as 1-oxides of such compounds, in which the ring double bond is in the 3,4-position, or salts of such compounds having salt-forming groups.

In ceph-2-em compounds, the optionally protected carboxyl group in the 4-position preferably has the α-configuration.

An amino protective group $R_1{}^A$ is a group which can be replaced by hydrogen, above all an acyl group Ac and also a triarylmethyl group, especially the trityl group, as well as an organic silyl group or an organic stannyl group. A group Ac above all represents the acyl radical of an organic carboxylic acid, preferably with up to 18 carbon atoms, especially the acyl radical of an optionally substituted aliphatic, cycloaliphatic, cycloaliphatic-aliphatic, aromatic, araliphatic, heterocyclic or heterocyclic-aliphatic carboxylic acid (including formic acid) as well as the acyl radical of a carbonic acid half-derivative.

A bivalent amino protective group formed by the radicals $R_1{}^A$ and $R_1{}^b$ together is in particular the bivalent acyl radical of an organic dicarboxylic acid, preferably with up to 18 carbon atoms, above all the diacyl radical of an aliphatic or aromatic dicarboxylic acid, and also the acyl radical of an α-aminoacetic acid which is preferably substituted in the α-position and contains, for example, an aromatic or heterocyclic radical, and wherein the amino group is bonded to the nitrogen atom via a methylene radical which is preferably substituted, for example which contains two lower alkyl groups, such as methyl groups. The radicals $R_1{}^A$ and $R_1{}^b$ can together also represent an organic ylidene radical, such as an aliphatic, cycloaliphatic, cycloaliphatic-aliphatic or araliphatic ylidene radical, preferably with up to 18 carbon atoms.

A protected carboxyl group of the formula —C(=O)—O—$R_2{}^A$ is above all an esterified carboxyl group, but can also represent an anhydride group, usually a mixed anhydride group.

The group $R_2{}^A$ can represent an organic radical, preferably with 18 carbon atoms, which together with the —C(=O)—O— grouping forms an esterified carboxyl group which can preferably be split easily; such radicals are, for example, aliphatic, cycloaliphatic, cycloaliphatic-aliphatic, aromatic or araliphatic radicals, especially optionally substituted hydrocarbon radicals of this nature, as well as heterocyclic or heterocyclic-aliphatic radicals.

The group $R_2{}^A$ can also represent an organic silyl radical, as well as an organo-metallic radical, such as an appropriate organic stannyl radical, especially a silyl or stannyl radical substituted by 1 to 3 optionally substituted hydrocarbon radicals, preferably with up to 18 carbon atoms, such as aliphatic hydrocarbon radicals.

A radical $R_2{}^A$ which forms an anhydride group, above all a mixed anhydride group, with the —C(=O)—O— group is especially the acyl radical of an organic carboxylic acid, preferably with 18 carbon atoms, such as of an aliphatic, cycloaliphatic, cycloaliphatic-aliphatic, aromatic or araliphatic carboxylic acid or of a carbonic acid half-derivative, such as a carbonic acid half-ester.

The general terms used in the preceding and following description for example have the following meanings:

An aliphatic radical, including the aliphatic radical of an appropriate organic carboxylic acid, as well as an appropriate ylidene radical, is an optionally substituted monovalent or divalent aliphatic hydrocarbon radical, especially lower alkyl, lower alkenyl or lower alkinyl, and also lower alkylidene, which can contain, for example, up to 7 and preferably up to 4 carbon atoms. Such radicals can optionally be monosubstituted, disubstituted or polysubstituted by functional groups, for example by free, etherified or esterified hydroxyl or mercapto groups, such as lower alkoxy, lower alkenyloxy, lower alkylenedioxy, optionally substituted phenyloxy or phenyl-lower alkoxy, lower alkylthio or optionally substituted phenylthio or phenyl-lower alkylthio, optionally substituted lower alkoxycarbonyloxy or lower alkanoyloxy, or halogen, and also by oxo, nitro, optionally substituted amino, for example di-lower alkylamino, lower alkyleneamino, oxa-lower alkyleneamino or aza-lower alkyleneamino as well as acylamino, such as lower alkanoylamino, optionally substituted carbamoylamino, ureidocarbonylamino or guanidinocarbonylamino, azido, acyl, such as lower alkanoyl or benzoyl, optionally functionally modified carboxyl, such as carboxyl present in the form of a salt, esterified carboxyl, such as lower alkoxycarbonyl, optionally substituted carbamoyl, such as N-lower alkylcarbamoyl or N,N-di-lower alkylcarbamoyl, and also optionally substituted ureidocarbonyl or guanidinocarbonyl, or cyano or optionally functionally modified sulpho, such as sulphamoyl or sulpho present in the salt form.

The divalent aliphatic radical of an aliphatic carboxylic acid is, for example, lower alkylene or lower alkenylene, which can optionally be monosubstituted, disubstituted or polysubstituted, for example like an aliphatic radical mentioned above.

A cycloaliphatic or cycloaliphatic-aliphatic radical, including the cycloaliphatic or cycloaliphaticaliphatic radical in an appropriate organic carboxylic acid or an appropriate cycloaliphatic or cycloaliphaticaliphatic ylidene radical is an optionally substituted, monovalent or divalent, cycloaliphatic or cycloaliphaticaliphatic hydrocarbon radical, for example monocyclic, bicyclic or polycyclic cycloalkyl or cycloalkenyl, or cycloalkylidene, or cycloalkyl- or cycloalkenyl-lower alkyl or -lower alkenyl, or cycloalkyl-lower alkylidene or cycloalkenyl-lower alkylidene, wherein cycloalkyl and cycloalkylidene for example contain up to 12, such as 3–8, preferably 3–6, ring carbon atoms, whilst cycloalkenyl can for example contain up to 12, such as 3–8, for example 5–8, preferably 5 or 6, ring carbon atoms as well as 1 to 2 double bonds, and the aliphatic part of a cycloaliphaticaliphatic radical can for example contain up to 7, preferably up to 4, carbon atoms. The above cycloaliphatic or cycloaliphatic-aliphatic radicals can, if desired, be monosubstituted, disubstituted or polysubstituted, for example by optionally substituted aliphatic hydrocarbon radicals, such as by the abovementioned optionally substituted lower alkyl groups, or by functional groups, for example like the abovementioned aliphatic hydrocarbon radicals.

The aromatic radical, including the aromatic radical of an appropriate carboxylic acid, is an optionally substituted aromatic hydrocarbon radical, for example a monocyclic, bicyclic or polycyclic aromatic hydrocarbon radical, especially phenyl, as well as biphenylyl or naphthyl, which can optionally be monosubstituted, disubstituted or polysubstituted, for example like the abovementioned aliphatic and cycloaliphatic hydrocarbon radicals.

The divalent aromatic radical of an aromatic carboxylic acid is above all 1,2-arylene, especially 1,2-phenylene, which can optionally be monosubstituted, disubstituted or polysubstituted, for example like the abovementioned aliphatic and cycloaliphatic hydrocarbon radicals.

The araliphatic radical, including the araliphatic radical in an appropriate carboxylic acid, as well as an araliphatic ylidene radical, is, for example, an optionally substituted araliphatic hydrocarbon radical, such as an optionally substituted aliphatic hydrocarbon radical, for example an aliphatic hydrocarbon radical possessing up to three optionally substituted monocyclic, bicyclic or polycyclic aromatic hydrocarbon radicals, and above all represents phenyl-lower alkyl or phenyl-lower alkenyl as well as phenyl-lower alkinyl or phenyl-lower alkylidene, and such radicals can, for example, contain 1–3 phenyl groups and can optionally be monosubstituted, disubstituted or polysubstituted in the aromatic and/or aliphatic part, for example like the abovementioned aliphatic and cycloaliphatic radicals.

Heterocyclic groups, including those in heterocyclic-aliphatic radicals, and including heterocyclic or heterocyclic-aliphatic groups in appropriate carboxylic acids, are especially monocyclic, as well as bicyclic or polycyclic, aza-, thia-, oxa-, thiaza-, thiadiaza-, oxaza-, diaza-, triaza- or tetraza-cyclic radicals of aromatic character, and also appropriate partially or completely saturated radicals, and these heterocyclic radicals can optionally be monosubstituted, disubstituted or polysubstituted, for example like the abovementioned cycloaliphatic radicals. The aliphatic part in heterocyclicaliphatic radicals for example has the meaning given for the appropriate cycloaliphatic-aliphatic or araliphatic radicals.

The acyl radical of a carbonic acid half-derivative is preferably the acyl radical of an appropriate half-ester, wherein the organic radical of the ester group represents an optionally substituted aliphatic, cycloaliphatic, aromatic or araliphatic hydrocarbon radical or a heterocyclicaliphatic radical, above all the acyl radical of a lower alkyl half-ester of carbonic acid which is optionally substituted, for example in the α- or β-position, or of a lower alkenyl, cycloalkyl, phenyl or phenyl-lower alkyl half-ester of carbonic acid which is optionally substituted in the organic radical. Acyl radicals of a carbonic acid half-ester are furthermore appropriate radicals of lower alkyl half-esters of carbonic acid in which the lower alkyl part contains a heterocyclic group, for example one of the abovementioned heterocyclic groups of aromatic character, and both the lower alkyl radical and the heterocyclic group can optionally be substituted. The acyl radical of a carbonic acid half-derivative can also be an optionally N-substituted carbamoyl group, such as an optionally halogenated N-lower alkylcarbamoyl group.

Lower alkyl is, for example, methyl, ethyl, n-propyl, isopropyl, n-butyl, isobutyl, sec.-butyl or tert.-butyl as well as n-pentyl, isopentyl, n-hexyl, isohexyl or n-heptyl, whilst lower alkenyl can be, for example, vinyl, allyl, isopropenyl, 2- or 3-methallyl or 3-butenyl, lower alkinyl can be, for example, propargyl or 2-butinyl and lower alkylidene can be, for example, isopropylidene or isobutylidene.

Lower alkylene is, for example, 1,2-ethylene, 1,2-or 1,3-propylene or 1,4-butylene, whilst lower alkenylene is, for example, 1,2-ethenylene or 2-buten-1,4-ylene.

Cycloalkyl is, for example, cyclopropyl, cyclobutyl, cyclopentyl, cyclohexyl or cycloheptyl, as well as adamantyl, cycloalkenyl is, for example, cyclopropenyl, 1-, 2- or 3-cyclopentenyl, 1-, 2- or 3-cyclohexenyl, 3-cycloheptenyl or 1,4-cyclohexadienyl, and cycloalkylidene is, for example, cyclopentylidene or cyclohexylidene. Cycloalkyl-lower alkyl or cycloalkyl-lower alkenyl is, for example, cyclopropyl-, cyclopentyl-, cyclohexyl- or cycloheptyl-methyl, 1,1- or 1,2-ethyl, 1,1-, 1,2- or 1,3-propyl, -vinyl or -allyl, whilst cycloalkenyl-lower alkyl or -lower alkenyl for example represents 1-, 2- or 3-cyclopentenyl-, 1-, 2- or 3-cyclohexenyl- or 1-, 2- or 3-cycloheptenylmethyl, -1,1- or -1,2-ethyl, -1,1-, -1,2- or -1,3-propyl, -vinyl or -allyl. Cycloalkyl-lower alkylidene is, for example, cyclohexylmethylene, and cycloalkenyl-lower alkylidene is, for example, 3-cyclohexenylmethylene.

Naphthyl is 1- or 2-naphthyl, whilst biphenylyl for example represents 4-biphenylyl.

Phenyl-lower alkyl or phenyl-lower alkenyl is, for example, benzyl, 1- or 2-phenylethyl, 1-, 2- or 3-phenylpropyl, diphenylmethyl, trityl, 1- or 2-naphthylmethyl, styryl or cinnamyl and phenyl-lower alkylidene is, for example, benzylidene.

Heterocyclic radicals are above all optionally substituted heterocyclic radicals of aromatic character, for example appropriate monocyclic, monoazacyclic, monothiacyclic or monooxacyclic radicals, such as pyrryl, for example 2-pyrryl or 3-pyrryl, pyridyl, for example 2-, 3- or 4-pyridyl, pyridinium, thienyl, for example 2- or 3-thienyl, or furyl, for example 2-furyl, bicyclic monoazacyclic, monooxacyclic or monothiacyclic radicals, such as indolyl, for example 2- or 3-indolyl, quinolinyl, for example 2- or 4-quinolinyl, isoquinolinyl, for example 1-isoquinolinyl, benzofuranyl, for example 2- or 3-benzofuranyl, or benzothienyl, for example 2- or 3-benzothienyl, monocyclic diazacyclic, triazacyclic, tetrazacyclic, thiazacyclic, thiadiazacyclic or oxazacyclic radicals, such as imidazolyl, for example 2-imidazolyl, pyrimidinyl, for example 2- or 4-pyrimidinyl, triazolyl, for example 1,2,4-triazol-3-yl, tetrazolyl, for example 1- or 5-tetrazolyl, oxazolyl, for example 2-oxazolyl, isoxazolyl, for example 3-isoxazolyl, thiazolyl, for example 2-thiazolyl, isothiazolyl, for example 3-isothiazolyl or 1,2,4- or 1,3,4-thiadiazolyl, for example 1,2,4-thiadiazol-3-yl or 1,3,4-thiadiazol-2-yl, or bicyclic diazacyclic, thiazacyclic or oxazacyclic radicals, such as benzimidazolyl, for example 2-benzimidazolyl, benzoxazolyl, for example 2-benzoxazolyl, or benzthiazolyl, for example 2-benzthiazolyl. Appropriate partially or completely saturated radicals are, for example, tetrahydrothienyl, such as 2-tetrahydrothienyl, tetrahydrofuryl, such as 2-tetrahydrofuryl, or piperidyl, for example 2- or 4-piperidyl. Heterocyclic-aliphatic radicals are lower alkyl or lower alkenyl containing heterocyclic groups, especially those mentioned above. The above-mentioned heterocyclyl radicals can, for example, by substituted by optionally substituted aliphatic hydrocarbon radicals, especially lower alkyl, such as methyl, or, for example like the aliphatic hydrocarbon radicals, by functional groups.

Lower alkoxy is, for example, methoxy, ethoxy, n-propoxy, isopropoxy, n-butoxy, isobutoxy, sec.-butoxy, tert.-butoxy, n-pentyloxy or tert.-pentyloxy. These groups can be substituted, for example as in halogen-lower alkoxy, especially 2-halogen-lower alkoxy, for example 2,2,2-trichloroethoxy, 2-bromoethoxy or 2-iodoethoxy. Lower alkenyloxy is, for example, vinyloxy or allyloxy, lower alkylenedioxy is, for example, methylenedioxy, ethylenedioxy or isopropylenedioxy, cycloalkoxy is, for example, cyclopentyloxy, cyclohexyloxy or adamantyloxy, phenyl-lower alkoxy is, for example benzyloxy or 1- or 2-phenylethoxy or heterocyclyloxy or heterocyclyl-lower alkoxy is, for example, pyridyl-lower alkoxy, such as 2-pyridylmethoxy, furyl-lower alkoxy, such as furfuryloxy, or thienyl-lower alkoxy, such as 2-thenyloxy.

Lower alkylthio is, for example, methylthio, ethylthio or n-butylthio, lower alkenylthio is, for example, allylthio, and phenyl-lower alkylthio is, for example, benzylthio, whilst mercapto groups etherified by heterocyclyl radicals or heterocyclyl-aliphatic radicals are in particular imidazolylthio, for example 2-imidazolylthio, thiazolylthio, for example 2-thiazolylthio, 1,2,4- or 1,3,4-thiadiazolylthio, for example 1,2,4-thiadiazol-3-ylthio or 1,3,4-thiadiazol-2-ylthio, or tetrazolylthio, for example 1-methyl-5-tetrazolylthio.

Esterified hydroxyl groups are above all halogen, for example fluorine, chlorine, bromine or iodine, as well as lower alkanoyloxy, for example acetoxy or propionyloxy, lower alkoxycarbonyloxy, for example methoxycarbonyloxy, ethoxycarbonyloxy or tert.-butoxycarbonyloxy, 2-halogenolower alkoxycarbonyloxy, for example 2,2,2-trichloroethoxycarbonyloxy, 2-bromoethoxycarbonyloxy or 2-iodoethoxycarbonyloxy, or phenylcarbonylmethoxycarbonyloxy, for example phenacyloxycarbonyloxy.

Lower alkoxycarbonyl is, for example, methoxycarbonyl, ethoxycarbonyl, n-propoxycarbonyl, isopropoxycarbonyl, tert.-butoxycarbonyl or tert.-pentyloxycarbonyl.

N-Lower alkyl- or N,N-di-lower alkyl-carbamoyl is, for example, N-methylcarbamoyl, N-ethylcarbamoyl, N,N-dimethylcarbamoyl or N,N-diethylcarbamoyl, whilst N-lower alkylsulphamoyl for example represents N-methylsulphamoyl or N,N-dimethylsulphamoyl.

Carboxyl or sulpho present in the form of an alkali metal salt is, for example, carboxyl or sulpho present in the form of a sodium or potassium salt.

Lower alkylamino or di-lower alkylamino is, for example, methylamino, ethylamino, dimethylamino or diethylamino, lower alkyleneamino is, for example, pyrrolidino or piperidino, oxa-lower alkyleneamino is, for example, morpholino, and aza-lower alkyleneamino is, for example, piperazino or 4-methylpiperazino. Acylamino in particular represents carbamoylamino, lower alkylcarbamoylamino, such as methylcarbamoylamino, ureidocarbonylamino, guanidinocarbonylamino, lower alkanoylamino, such as acetylamino or propionylamino, and also phthalimido or sulphoamino which is optionally present in the form of a salt, such as an alkali metal salt, for example a sodium salt or ammonium salt.

Lower alkanoyl is, for example, acetyl or propionyl.

Lower alkenyloxycarbonyl is, for example, vinyloxycarbonyl, whilst cycloalkoxycarbonyl and phenyl-lower alkoxycarbonyl for example represent adamantyloxycarbonyl, benzyloxycarbonyl, diphenylmethoxycarbonyl or α-4-biphenylyl-α-methyl-ethoxycarbonyl. Lower alkoxycarbonyl wherein lower alkyl for example contains a monocyclic, monoazacyclic, monoxacyclic or monothiacyclic group, is, for example, furyl-lower alkoxycarbonyl, such as furfuryloxycarbonyl, or thienyl-lower alkoxycarbonyl, for example 2-thenyloxycarbonyl.

An acyl group Ac in particular represents an acyl radical of an organic carboxylic acid or of a carbonic acid half-derivative contained in a naturally occurring or in a biosynthetically, semi-synthetically or fully synthetically obtainable, preferably pharmacologically active, N-acyl derivative of 6-amino-penicillanic acid or 7-amino-cephalosporanic acid compounds, or represents an easily removable acyl radical, especially of a carbonic acid half-derivative.

An acyl radical Ac contained in pharmacologically active N-acyl derivatives of 6-amino-penicillanic acid or 7-amino-cephalosporanic acid is above all a group of the formula

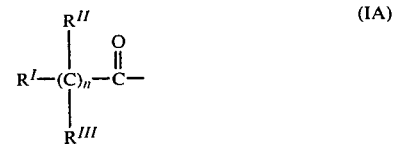

(IA)

wherein n represents 0 and $R^I$ denotes hydrogen or an optionally substituted cycloaliphatic or aromatic hydrocarbon radical, or an optionally substituted heterocyclic radical, preferably of aromatic character, a functionally modified, preferably etherified, hydroxyl or mercapto group or an optionally substituted amino group, or wherein n represents 1, $R^I$ represents hydrogen or an optionally substituted aliphatic, cycloaliphatic, cycloaliphaticaliphatic, aromatic or araliphatic hydrocarbon radical or an optionally substituted heterocyclic or heterocyclicaliphatic radical, wherein the heterocyclic radical preferably possesses aromatic character and/or a quaternary nitrogen atom, an optionally functionally modified, preferably etherified or esterified hydroxyl or mercapto group, an optionally functionally modified carboxyl group, an acyl group, an optionally substituted amino group or an azido group, and each of the radicals $R^{II}$ and $R^{III}$ denotes hydrogen, or wherein n represents 1, $R^I$ denotes an optionally substituted aliphatic, cycloaliphatic, cycloaliphatic-aliphatic, aromatic or araliphatic hydrocarbon radical or an optionally substituted heterocyclic or heterocyclic-aliphatic radical, wherein the heterocyclic radical preferably possesses aromatic character, $R^{II}$ denotes an optionally functionally modified, preferably etherified hydroxyl or mercapto group, an optionally substituted amino group, an optionally functionally modified carboxyl group or sulpho group, an azido group or a halogen atom and $R^{III}$ represents hydrogen, or wherein n represents 1, each of the radicals $R^I$ and $R^{II}$ denotes a functionally modified, preferably etherified or esterified, hydroxyl group or an optionally functionally modified carboxyl group, and $R^{III}$ represents hydrogen, or wherein n represents 1, $R^I$ denotes hydrogen or an optionally substituted aliphatic, cycloaliphatic, cycloaliphatic-aliphatic, aromatic or araliphatic hydrocarbon radical and $R^{II}$ and $R^{III}$ together represent an optionally substituted aliphatic, cyclo-aliphatic, cycloaliphatic-aliphatic or araliphatic hydrocarbon radical bonded to the carbon atom by a double bond, or wherein n represents 1 and $R^I$ denotes an optionally substituted aliphatic, cycloaliphatic, cycloaliphatic-aliphatic, aromatic or araliphatic hydrocarbon radical or an optionally substituted heterocyclic or heterocyclic-aliphatic radical, wherein heterocyclic radicals preferably possess aromatic character, $R^{II}$ denotes an optionally substituted aliphatic, cycloaliphatic, cycloaliphatic-aliphatic, aromatic or araliphatic hydrocarbon radical and $R^{III}$ denotes hydrogen or an optionally substituted aliphatic, cycloaliphatic, cycloaliphatic-aliphatic, aromatic or araliphatic hydrocarbon radical.

In the abovementioned acyl groups of the formula IA, for example, n represents O and $R^I$ represents hydrogen or a cycloalkyl group with 5–7 ring carbon atoms optionally substituted, preferably in the 1-position, by amino or by a sulphoamino group which is optionally present in the salt form, for example the alkali metal salt form, a phenyl, naphthyl or tetrahydronaphthyl group which is optionally substituted, preferably by hydroxyl, lower alkoxy, for example methoxy and/or halogen, for example chlorine, a heterocyclic group which is optionally substituted, for example by lower alkyl and/or phenyl, which can in turn carry substituents, such as halogen, for example chlorine, such as a 4-isoxazolyl group, or an amino group which is preferably N-substituted, for example by a lower alkyl radical which is optionally substituted such as a lower alkyl radical containing halogen, for example chlorine, or n represents 1, $R^I$ represents a lower alkyl group which is optionally substituted, preferably by halogen, such as chlorine, optionally substituted phenyloxy, such as phenyloxy containing hydroxyl and/or halogen, for example chlorine, amino or carboxyl, a lower alkenyl group, an optionally substituted phenyl group, such as a phenyl group containing hydroxyl, halogen, for example chlorine, and/or optionally substituted phenyloxy, such as phenyloxy containing hydroxyl and/or halogen, for example chlorine, a pyridyl, pyridinium, thienyl, 1-imidazolyl or 1-tetrazolyl group which is optionally substituted, for example by lower alkyl, such as methyl, amino or aminomethyl, an optionally substituted lower alkoxy group, for example a methoxy group, a phenyloxy group which is optionally substituted, for example by hydroxyl and/or halogen, such as chlorine, a lower alkylthio group, for example a n-butylthio group, or a lower alkenylthio group, for example an allylthio group, an optionally substituted, for example lower alkyl-substituted such as methyl-substituted, phenylthio, 2-imidazolylthio, 1,2,4-triazol-3-ylthio, 1,3,4-triazol-2-ylthio, 1,2,4-thiadiazol-3-ylthio, such as 5-methyl-1,2,4-thiadiazol-3-ylthio, 1,3,4-thiadiazol-2-ylthio, such as 5-methyl-1,3,4-thiadiazol-2-ylthio, or 5-tetrazolylthio, such as 1-methyl-5-tetrazolylthio, group, a halogen atom, especially a chlorine or bromine atom, an optionally functionally modified carboxyl group, such as lower alkoxycarbonyl, for example methoxycarbonyl or ethoxycarbonyl, cyano or carbamyl which is optionally N-substituted, for example by lower alkyl, such as methyl or phenyl, an optionally substituted lower alkanoyl group, for example an acetyl or propionyl or benzoyl group, or an azido group, and $R^{II}$ and $R^{III}$ represent hydrogen, or n represents 1, $R^I$ represents a phenyl or thienyl group which is optionally substituted, for example by hydroxyl and/or halogen, for example chlorine, or represents a 1,4-cyclohexadienyl group, $R^{II}$ represents optionally substituted amino, such as lower alkoxycarbonylamino or 2-halogeno-lower alkoxycarbonylamino, for example tert.-butoxycarbonylamino or 2,2,2-trichloroethoxycarbonylamino, or optionally substituted carbamoylamino, such as guanidinocarbonylamino, or a sulphoamino group optionally present in the salt form, for example the alkali metal salt form, an azido group, a carboxyl group optionally present in the salt form, for example the alkali metal salt form, or in the esterified form, for example as a lower alkoxycarbonyl, for example methoxycarbonyl or ethoxycarbonyl, group, a cyano group, a sulpho group, optionally functionally modified hydroxyl, such as lower alkoxycarbonyloxy or 2-halogeno-lower alkoxycarbonyloxy, for example tert.-butoxycarbonyloxy or 2,2,2-trichlorocarbonyloxy, or optionally substituted lower alkoxy or phenyloxy, or a halogen atom, for example chlorine or bromine, and $R^{III}$ represents hydrogen, or n represents 1, $R^I$ and $R^{II}$ each represents halogen, for example bromine, or lower alkoxycarbonyl, for example methoxycarbonyl, and $R^{III}$ represents hydrogen, or n represents 1 and each of the groups $R^I$, $R^{II}$ and $R^{III}$ represents lower alkyl, for example methyl.

Such acyl radicals Ac are, for example, formyl, cyclopentylcarbonyl, α-aminocyclopentylcarbonyl or α-aminocyclohexylcarbonyl (with an optionally substituted amino group, for example a sulphoamino group optionally present in the form of a salt, or an amino group substituted by an acyl radical which can be split off, preferably easily, for example on treatment with an acid agent, such as trifluoroacetic acid, or with a chemical reducing agent, such as zinc in the presence of aqueous acetic acid, or substituted by an acyl radical which can be converted into such a radical, preferably a suitable acyl radical of a carbonic acid half-ester, such as 2,2,2-trichloroethoxycarbonyl, 2-bromoethoxycarbonyl, 2-iodoethoxycarbonyl, tert.-butoxycarbonyl, phenacyloxycarbonyl or of a carbonic acid halfamide, such as carbamoyl or N-methylcarbamoyl, as well as by trityl), 2,6-dimethoxybenzoyl, tetrahydronaphthoyl, 2-methoxy-naphthoyl, 2-ethoxy-naphthoyl, benzyloxycarbonyl, hexahydrobenzyloxycarbonyl, 5-methyl-3-phenyl-4-isoxazolylcarbonyl, 3-(2-chlorophenyl)-5-methyl-4-isooxazolylcarbonyl, 3-(2,6-dichlorophenyl)-5-methyl-4-isoxazolylcarbonyl, 2-chloroethylaminocarbonyl, acetyl, propionyl, butyryl, hexanoyl, octanoyl, acrylyl, crotonoyl, 3-butenoyl, 2-pentenoyl, methoxyacetyl, methylthioacetyl, butylthioacetyl, allylthioacetyl, chloroacetyl, bromoacetyl, dibromoacetyl, 3-chloropropionyl, 3-bromopropionyl, aminoacetyl or 5-amino-5-carboxyl-valeryl (with an amino group which is optionally substituted, for example as indicated, and/or a carboxyl group which is optionally functionally modified, for example present in the form of a salt, such as a sodium salt, or in the form of an ester, such as a lower alkyl ester, for example a methyl or ethyl ester), azidoacetyl, carboxyacetyl, methoxycarbonylacetyl, ethoxycarbonylacetyl, bismethoxycarbonylacetyl, N-phenylcarbamoylacetyl, cyanoacetyl, α-cyanopropionyl, 2-cyano-3,3-dimethylacrylyl, phenylacetyl, α-bromophenylacetyl, α-azido-phenylacetyl, 3-chlorophenylacetyl, 4-aminomethylphenyl-acetyl, (with an amino group which is optionally substituted, for example as indicated), phenacylcarbonyl, phenyloxyacetyl, 4-trifluoromethyl-phenyloxyacetyl, benzyloxyacetyl, phenylthioacetyl, bromophenylthioacetyl, 2-phenyloxypropionyl, α-phenyloxyphenylacetyl, α-hydroxyphenylacetyl, α-methoxy-phenylacetyl, α-ethoxyphenylacetyl, α-methoxy-3,4-dichlorophenylacetyl, α-cyano-phenylacetyl, especially phenylglycyl, 4-hydroxyphenylglycyl, 3-chloro-4-hydroxy-phenylglycyl or 3,5-sichloro-4-hydroxy-phenylglycyl, (the amino group in these radicals being optionally substituted, for example as indicated above), also benzylthioacetyl, benzylthiopropionyl, α-carboxyphenylacetyl (with a carboxyl group which is optionally functionally modified, for example as indicated above), 3-phenylpropionyl, 3-(3-cyanophenyl)-propionyl, 4-(3-methoxyphenyl)-butyryl, 2-pyridylacetyl, 4-aminopyridiniumacetyl (optionally with an amino group which is substituted, for example as indicated above), 2-thienylacetyl, 2-tetrahydrothienylacetyl, α-carboxy-2-thienylacetyl or α-carboxy-3-thienylacetyl (optionally with a carboxyl group which is functionally modified, for example as indicated above), α-cyano-2-thienylacetyl, α-amino-2-thienylacetyl or α-amino-3-thienylacetyl (optionally with an amino group which is substituted, for example as indicated above), α-sulpho-phenylacetyl (optionally with a sulpho group which is functionally modified, for example like the carboxyl group), 3-thienylacetyl, 2-furylacetyl, 1-imidazolylacetyl, 1-tetrazolylacetyl, 3-methyl-2-imidazolylthioacetyl, 1,2,4-triazol-3-ylthioacetyl, 1,3,4-triazol-2-ylthioacetyl, 5-methyl-1,2,4-thiadiazol-3-ylthioacetyl, 5-methyl-1,3,4-thiadiazol-2-ylthioacetyl or 1-methyl-5-tetrazolylthioacetyl.

An easily removable acyl radical Ac, especially of a carbonic acid half-ester, is above all an acyl radical of a half-ester of carbonic acid which can be split off by reduction, for example on treatment with a chemical reducing agent, or by treatment with acid, for example with trifluoroacetic acid, such as a lower alkoxycarbonyl radical which, preferably in the α-position, is multiple-branched or substituted by acylcarbonyl radicals, especially benzoyl radicals, or which is substituted in the β-position by halogen atoms, for example tert.-butoxycarbonyl, tert.-pentyloxycarbonyl, phenacyloxycarbonyl, 2,2,2-trichloroethoxycarbonyl and 2-iodoethoxycarbonyl or a radical which can be converted into the latter, such as 2-chloro- or 2-bromo-ethoxycarbonyl and also preferably polycyclic cycloalkoxycarbonyl, for example adamantyloxycarbonyl, optionally substituted phenyl-lower alkoxycarbonyl, above all α-phenyl-lower alkoxycarbonyl, wherein the α-position preferably is multiple-substituted, for example diphenylmethoxycarbonyl or α-4-biphenylyl-α-methyl-ethyloxycarbonyl or furyl-lower alkoxycarbonyl, above all α-furyl-lower alkoxycarbonyl, for example furfuryloxycarbonyl.

A bivalent acyl radical formed by the two radicals $R_1^A$ and $R_1^b$ is, for example, the acyl radical of a lower alkanedicarboxylic or lower alkenedicarboxylic acid, such as succinyl, or of a o-aryldicarboxylic acid, such as phthaloyl.

A further bivalent radical formed by the groups $R_1^A$ and $R_1^b$ is, for example, a 1-oxo-3-aza-1,4-butylene radical which is substituted, especially in the 2-position, and for example contains optionally substituted phenyl or thienyl and is optionally monosubstituted or disubstituted in the 4-position by lower alkyl, such as methyl, for example 4,4-dimethyl-2-phenyl-1-oxo-3-aza-1,4-butylene.

An organic radical $R_2^A$ which together with the —C(=O)—O— grouping forms an esterified carboxyl group which can preferably be split easily represents, for example, a 2-halogeno-lower alkyl radical $R_2^a$, wherein halogen preferably has an atomic weight of above 19. Such a radical forms, together with the —C(=O)—O— grouping, an esterified carboxyl group which can easily be split on treatment with chemical reducing agents under neutral or weakly acid conditions, for example with zinc in the presence of aqueous acetic acid, or an esterified carboxyl group which can easily be converted into such a group, and is, for example, 2,2,2-trichloroethyl or 2-iodoethyl, or 2-chloroethyl or 2-bromoethyl, which can easily be converted into the latter.

A further group $R_2^A$ which together with the —C(=O)—O— grouping also represents an esterified carboxyl group which can easily be split on treatment with chemical reducing agents under neutral or weakly acid conditions, for example on treatment with zinc in the presence of aqueous acetic acid and also on treatment with a suitable nucleophilic reagent, for example sodium thiophenolate, is an arylcarbonylmethyl group $R_2^b$, wherein aryl especially represents an optionally substituted phenyl group, and preferably phenacyl.

The group $R_2^A$ can also represent the radical $R_2^c$, which represents an arylmethyl group, wherein aryl especially denotes a monocyclic, preferably substituted aromatic hydrocarbon radical. Such a radical together with the —C(=O)—O— grouping forms an esterified carboxyl group which can easily be split on irradiation, preferably with ultraviolet light, under neutral or acid conditions. Such an aryl radical contains, as substituents, especially lower alkoxy, for example methoxy (which in the preferred phenyl radical are above all in the 3-, 4- and/or 5-position) and/or above all nitro (preferably in the 2-position in the preferred phenyl radical). Such radicals $R_2^c$ are above all 3- or 4-methoxybenzyl, 3,5-dimethoxy-benzyl, 2-nitrobenzyl or 4,5-dimethoxy-2-nitro-benzyl.

A group $R_2^A$ can also represent the radical $R_2^d$ which together with the —C(=O)—O— grouping forms an esterified carboxyl group which can easily be split under acid conditions, for example on treatment with trifluoroacetic acid or formic acid. Such a radical $R_2^d$ is above all a methyl group which is polysubstituted by optionally substituted hydrocarbon radicals or is monosubstituted by a carbocyclic aryl group possessing electron-donating substituents or a heterocyclic group of aromatic character possessing oxygen or sulphur atoms as ring members, or denotes a ring member in a polycycloaliphatic hydrocarbon radical or denotes the ring member representing the α-position to the oxygen atom or sulphur atom in an oxacycloaliphatic or thiacycloaliphatic radical.

Preferred polysubstituted methyl groups $R_2^d$ are, for example, tert.-butyl, tert.-pentyl, benzhydryl, 4,4'-dimethoxy-benzyhydryl or 2-(4-biphenylyl)-2-propyl, whilst a methyl group $R_2^d$ containing the abovementioned substituted aryl group or the heterocyclic group is, for example, 4-methoxybenzyl or 3,4-dimethoxy-benzyl or 2-furyl. A polycycloaliphatic hydrocarbon radical in which the methyl group $R_2^d$ represents a preferably triply branched ring member is, for example, adamantyl, such as 1-adamantyl, and an abovementioned oxacycloaliphatic or thiacycloaliphatic radical $R_2^d$ is 2-tetrahydrofuryl, 2-tetrahydropropyranyl or 2,3-dihydro-2-pyranyl or corresponding sulphur analogues.

The radical $R_2^A$ can also represent a radical $R_2^e$ which together with the —C(=O)—O— grouping forms an esterified carboxyl group which can be split hydrolytically, for example under weakly basic or weakly acid conditions. Such a radical $R_2^e$ is, preferably, a radical which forms an activated ester with the —C(=O)—O— grouping, such as nitrophenyl, for example 4-nitrophenyl or 2,4-dinitrophenyl, nitrophenyl-lower alkyl, for example 4-nitrobenzyl, polyhalogenophenyl, for example 2,4,6-trichlorophenyl or 2,3,4,5,6-pentachlorophenyl, also cyanomethyl and acylaminomethyl, for example phthaliminomethyl or succinyliminomethyl.

The group $R_2^A$ can also represent a radical $R_2^f$ which together with the carboxyl group —C(=O)—O— forms an esterified carboxyl group which can be split under hydrogenolytic conditions and is, for example, an optionally substituted α-aryl-lower alkyl radical, such as benzyl, 4-methoxy-benzyl, 4-nitrobenzyl, benzhydryl or 4,4-dimethoxybenzhydryl.

The group $R_2^A$ can also represent a radical $R_2^g$ which together with the carboxyl grouping —C(=O)—O— forms an esterified carboxyl group which can be split under physiological conditions, above all lower alkanoyloxymethyl, for example acetoxymethyl.

A silyl or stannyl radical $R_2^A$ preferably contains optionally substituted aliphatic, cycloaliphatic, aromatic or araliphatic hydrocarbon radicals, such as lower alkyl, cycloalkyl, phenyl or phenyl-lower alkyl groups, and above all represents tri-lower alkylsilyl, for example trimethylsilyl, or tri-lower alkylstannyl, for example tri-n-butylstannyl.

An acyl radical which together with the —C(=O)—O— grouping forms a mixed anhydride group which can be split, preferably hydrolytically, is, for example, the acyl radical of one of the abovementioned organic carboxylic acids or carbonic acid half-derivatives, such as lower alkanoyl, for example acetyl, or lower alkoxycarbonyl, for example ethoxycarbonyl.

Salts are especially those of compounds of the formula I in which $R_2$ represents hydrogen and above all metal salts or ammonium salts, such as alkali metal and alkaline earth metal salts, for example sodium, potassium, magnesium or calcium salts, as well as ammonium salts with ammonia or suitable organic amines, with above all aliphatic, cycloaliphatic, cycloaliphatic-aliphatic and araliphatic primary, secondary or tertiary monoamines, diamines or polyamines, as well as heterocyclic bases being used for salt formation, such as lower alkylamines, for example triethylamine, hydroxy-lower alkylamines, for example 2-hydroxyethylamine, bis-(2-hydroxyethyl)-amine or tri-(2-hydroxyethyl)-amine, basic aliphatic esters of carboxylic acids, for example 4-aminobenzoic acid 2-diethylaminoethyl ester, lower alkyleneamines, for example 1-ethyl-piperidine, cycloalkylamines, for example bicyclohexylamine, or benzylamines, for example N,N'-dibenzyl-ethylenediamine, and also bases of the pyridine type, for example pyridine, collidine or quinoline. Compounds of the formula I in which, for example, $R_1^a$ and $R_1^b$ represent hydrogen, or which possess a basic group in a radical $R_1^a$ and $R_1^b$, can also form acid addition salts, for example with inorganic acids, such as hydrochloric acid, sulphuric acid or phosphoric acid, or with suitable organic carboxylic or sulphonic acids, for example trifluoroacetic acid. Compounds of the formula I wherein $R_2$ represents hydrogen and in which $R_1^a$ and $R_1^b$ denote hydrogen, or which contain a basic group in a radical $R_1^a$ and $R_1^b$, can also be present in the form of an internal salt, that is to say in the form of a zwitter-ion.

The compounds of the formula I possess valuable pharmacological properties or can be used as intermediate products for the manufacture of such compounds. Compounds of the formula I wherein $R_1^a$ denotes an acyl radical Ac which occurs in pharmacologically active N-acyl derivatives of 6-amino-penam-3-carboxylic acid compounds or 7-aminoceph-3-em-4-carboxylic acid compounds and $R_1^b$ represents hydrogen, and $R_2$ denotes hydrogen or an organic radical $R_2^A$ which can easily be split off under physiological conditions, and in which the double bond is in the 3,4-position of the cephem ring, are active against micro-organisms, such as Gram-positive bacteria, for example *Staphylococcus aureus* (for example, in mice at doses of about 0.001 to about 0.02 g/kg p.o.) and Gram-negative bacteria, for example *Escherichia coli* (for example, in mice at doses of about 0.001 to about 0.05 g/kg p.o.), furthermore *Klebsiella pneumoniae*, *Proteus vulgaris* or *Salmonella typhosa*, and especially also against penicillin-resistant bacteria. The new compounds can therefore be used accordingly, for example in the form of antibiotically active preparations.

Compounds of the formula I wherein the double bond of the cephem ring occupies the 2,3-position, and $R_1^a$, $R_1^b$ and $R_2$ have the meanings indicated in connection with the formula I, or wherein the double bond of the cephem ring occupies the 3,4-position and the radicals $R_1^a$ and $R_1^b$ represent hydrogen or $R_1^a$ denotes an amino protective group different from the abovementioned acyl radical and $R_1^b$ represents hydrogen, or $R_1^A$ and $R_1^b$ together represent a divalent amino protective group and $R_2$ represents hydrogen, or $R_1^a$ and $R_1^b$ have the abovementioned meanings and $R_2$ represents an organic radical $R_2^A$ which together with the —C(=O)—O— grouping forms an esterified carboxyl group which can preferably be split easily, are valuable intermediate products, which can in a simple manner, for example as described below, be converted into the abovementioned pharmacologically active compounds.

Particularly valuable compounds are ceph-3-em compounds of the formula I wherein $R_1^a$ denotes hydrogen or an acyl radical contained in a naturally occurring or biosynthetically, semi-synthetically or completely synthetically obtainable, especially pharmacologically active, such as highly active, N-acyl derivative of a 6-amino-penicillanic acid compound or 7-amino-cephalosporanic acid compound or an easily split-off acyl radical of a carbonic acid half-derivative, especially of a carbonic acid half-ester, $R_1^b$ represents hydrogen and $R_2$ represents hydrogen or an organic radical $R_2^A$, which together with the —C(=O)—O— grouping forms an esterified carboxyl group which can easily be split on treatment with water, with an acid agent, with a chemical reducing agent under neutral or weakly acid conditions, hydrolytically or hydrogenolytically, or an esterified carboxyl group which can easily be split under physiological conditions, or an esterified carboxyl group which can be converted into such a group, and, for example, represents trimethylsilyl, tert.-butyl, diphenylmethyl, 2,2,2-trichloroethyl, 2-chloroethyl, 2-bromoethyl, 2-iodoethyl, phenacyl, 4-methoxybenzyl, diphenylmethyl, 4,4'-dimethoxy-diphenylmethyl, 4-nitrobenzyl or acetonyl, as well as the corresponding ceph-2-em compounds, and also salts of such compounds having salt-forming groups.

Above all, in a ceph-3-em and ceph-2-em compound of the formula I, $R_1^a$ represents hydrogen or an acyl radical contained in fermentatively obtainable (that is to say naturally occurring) or biosynthetically obtainable N-acyl derivatives of 6-amino-penam-3-carboxylic acid compounds or 7-amino-ceph-3-em-4-carboxylic acid compounds, such as an optionally substituted phenylacetyl or phenyloxyacetyl radical, also an optionally substituted lower alkanoyl or lower alkenoyl radical, for example 4-hydroxy-phenylacetyl, hexanoyl, octanoyl, 3-hexenoyl, 5-amino-5-carboxy-valeryl, n-butylthioacetyl or allylthioacetyl, and especially phenylacetyl or phenyloxyacetyl, an acyl radical occurring in highly active N-acyl derivatives of 6-amino-penam-3-carboxylic acid compounds or 7-amino-ceph-3-em-4-carboxylic acid compounds, such as formyl, 2-chloroethylcarbamoyl, cyanoacetyl or 2-thienylacetyl, and especially phenylglycyl, wherein phenyl represents phenyl which is optionally substituted by hydroxyl and/or halogen, for example chlorine, for example phenyl or 3- or 4-hydroxy-, 3-chloro-4-hydroxy- or 3,5-dichloro-4-hydroxy-phenyl, and wherein the amino group is optionally substituted and for example represents a sulphoamino group which may be present in the salt form or an amino group which contains, as substituents, a hydrolytically removable trityl group or an optionally substituted carbamoyl group, such as an optionally substituted ureidocarbonyl group, for example ureidocarbonyl or $N^3$-trichloromethylureidocarbonyl, or an optionally substituted guanidinocarbonyl group, for example guanidinocarbonyl, or an acyl radical which can be split off, preferably easily, for example on treatment with an acid agent, such as trifluoroacetic acid, or with a chemical reducing agent, such as zinc in the presence of aqueous acetic acid, or an acyl radical which can be converted into such a radical, preferably a suitable acyl radical of a carbonic acid half-ester, such as 2,2,2-trichloroethyloxycarbonyl, 2-chloroethoxycarbonyl, 2-bromoethoxycarbonyl, 2-iodoethoxycarbonyl, tert.-butoxycarbonyl or phenacyloxycarbonyl, or of a carbonic acid half-amide, such as carbamoyl or N-methylcarbamoyl, or wherein the amino group is bonded to the nitrogen atom of the 7-amino group by a methylene group which optionally contains lower alkyl, such as two methyl, also thienylglycyl, such as 2-thienylglycyl (optionally with an amino group which is substituted, for example as indicated above), or 1-amino-cyclohexylcarbonyl (optionally with an amino group which is substituted, for example as indicated above), also α-carboxy-phenylacetyl or α-carboxy-2-thienylacetyl (optionally with a functionally modified carboxyl form, for example a carboxyl group present in the salt form, such as the sodium salt form, or in the ester form, such as the lower alkyl ester form, for example the methyl or ethyl ester form, or phenyl-lower alkyl ester form, for example diphenylmethyl ester form), α-sulphophenylacetyl (optionally with a sulpho group which is functionally modified, for example like the carboxyl group), or α-hydroxy-phenylacetyl (optionally with a functionally modified hydroxyl group, especially an acyloxy group, wherein acyl denotes an acyl radical which can be split off, preferably easily, for example on treatment with an acid agent, such as trifluoroacetic acid, or with a chemical reducing agent, such as zinc in the presence of aqueous acetic acid, or an acyl radical which can be converted into such a radical, preferably a suitable acyl radical of a carbonic acid half-ester, such as 2,2,2-trichloroethyloxycarbonyl, 2-chloroethoxycarbonyl, 2-bromoethoxycarbonyl, 2-iodoethoxycarbonyl, tert.-butoxycarbonyl or phenacyloxycarbonyl), for example an acyl radical of the formula IA, and also an acyl radical of a carbonic acid half-ester which can easily be split off, especially under acid conditions, for example on treatment with trifluoroacetic acid, or by reduction, for example with zinc in the presence of aqueous acetic acid, such as tert.-butoxycarbonyl, phenacylcarbonyl, 2,2,2-trichloroethoxycarbonyl or 2-iodoethoxycarbonyl, or 2-bromoethoxycarbonyl which can be converted into the latter, and $R_1^b$ represents hydrogen and $R_2$ represents hydrogen or a radical $R_2^A$, which together with the —C(=O)—O— grouping forms an esterified carboxyl group which can easily be split on treatment with a chemical reducing agent under neutral or weakly acid conditions, with an acid agent or, preferably under weakly basic conditions, hydrolytically, also hydrogenolytically or under physiological conditions, and above all methyl which is polysubstituted by optionally substituted hydrocarbon radicals, such as lower alkyl radicals, especially tert.-butyl or diphenylmethyl, as well as 2,2,2-trichloroethyl, 2-iodoethyl or 2-chloroethyl or 2-bromoethyl which can easily be converted into the latter, or phenacyl, as well as 4-methoxybenzyl or 4-nitrobenzyl, and also diphenylmethyl, 4,4'-dimethoxy-diphenylmethyl, trityl or bis-(4-methoxyphenyloxy)-methyl, as well as acetoxymethyl or pivaloyloxymethyl.

The reaction concerns above all the manufacture of compounds of the formula I, wherein $R_1^b$ denotes hydrogen, $R_1^a$ denotes hydrogen or an acyl group of the formula

wherein Ar represents phenyl, 3- or 4-hydroxyphenyl, 3-chloro-4-hydroxyphenyl, 3,5-dichloro-4-hydroxyphenyl or 2-thienyl, and wherein R represents hydrogen or optionally protected amino, carboxyl, sulpho or hydroxyl, such as acylamino, for example tert.-butoxycarbonylamino, 2,2,2-trichloroethoxycarbonylamino, 2-iodoethoxycarbonylamino, 2-bromoethoxycarbonylamino or 3-guanylureido, as well as sulphonamino or tritylamino, esterified carboxyl, such as diphenylmethoxycarbonyl, or acyloxy, for example tert.butoxycarbonyloxy, 2,2,2-trichloroethoxycarbonyloxy, 2-iodoethoxycarbonyloxy or 2-bromoethoxycarbonyloxy, or wherein $R_1^a$ denotes the acyl group of the formula Ia, in which Ar has the above meaning, and R represents an amino group which is bonded to $R_1^b$, which represents methylene or isopropylidene, and $R_2$ represents hydrogen, α-poly-branched lower alkyl, for example tert.-butyl, 2-halogeno-lower alkyl, for example 2,2,2-trichloroethyl, 2-iodoethyl or 2-bromoethyl, phenacyl, 4-nitrobenzyl or 4-methoxybenzyl, optionally substituted diphenylmethyl, for example benzhydryl or 4,4'-dimethoxy-diphenylmethyl, trityl or bis-(4-methoxy-phenyloxy)-methyl, and wherein the double bond of the cephem ring is preferably in the 3,4-position but also in the 2,3-position, or salts of such compounds possessing salt-forming groups.

It has now been found, surprisingly, that the compounds of the formula I can be obtained if in a 3-formyl-cephem-4-carboxylic acid compound of the formula

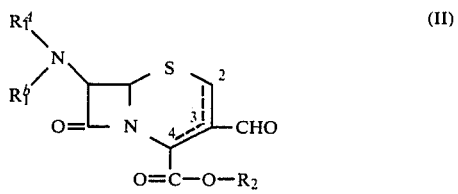

which contains a double bond in the 2,3- or 3,4-position, or in a 1-oxide of a ceph-3-em compound of the formula II, the formyl group is replaced by hydrogen and, if desired, in a compound obtainable an amino protective group $R_1^A$ is split off and/or, if desired, a resulting compound of the formula I is converted into another compound of the formula I, and/or, if desired, a resulting compound having a salt-forming group is converted into a salt or a resulting salt into the free compound or into another salt, and/or, if desired, a resulting isomer mixture is separated into the individual isomers.

In a starting material of the formula II, an amino protective group $R_2^A$ in particular represents an acyl group Ac, wherein free functional groups which may be present, for example amino, hydroxyl or carboxyl groups, can be protected in a manner which is in itself known, amino groups for example by acylation, tritylation, silylation or stannylation, and hydroxyl or carboxyl groups for example by esterification, including silylation or stannylation, and $R_1^b$ represents hydrogen, whilst $R_2$ above all, especially in ceph-3-em starting substances, represents a radical $R_2^A$ which forms, with the —C(=O)—O— grouping, a protected esterified carboxyl group which can preferably be split under mild conditions. Preferably, $R_2^A$ represents the organic radical of a sterically hindered alcohol, such as of a methanol containing optionally substituted aliphatic or aromatic hydrocarbon radicals. This methanol above all contains as substituents, three radicals of aliphatic character or 1 to 3, preferably 2, radicals of aromatic character. $R_2^A$ above all represents a diphenylmethyl radical which is optionally substituted, for example by lower alkoxy, such as methoxy, for example benzhydryl or 4,4'-dimethoxy-benzhydryl, but can also represent an optionally suitably substituted benzyl radical. The radical of a sterically hindered alcohol can also represent the radical of an α-poly-branched lower alkanol, for example a tert.-butyl group or of a cycloalkanol or cycloalkenol which optionally contains endo bridges; such radicals are, for example, adamantyl groups, such as 1-adamantyl. Preferably, free functional groups in an amino protective group $R_1^A$ and/or in an acyl radical $R_1^b$ and/or in a carboxyl protective group $R_2^A$ are protected in a manner which is in itself known.

The replacement of the formyl group by hydrogen in a starting material of the formula II is effected by decarbonylation. This reaction is above all carried out by treating the latter material with a heavy metal complex which takes up carbon monoxide. Such heavy metal complexes are especially platinum metal complexes, and by a platinum metal there is to be understood, apart from platinum, for example also iridium or rhodium, and also palladium and osmium. A platinum metal complex which takes up carbon monoxide preferably contains organic ligands; these can be bonded to the platinum metal atom by a carbon atom, as well as by a hetero-atom, especially a phosphorus atom, via the secondary valencies (which form non-covalent bonds) of the platinum metal atom. Apart from these organic ligands, the complex can also contain substituents bonded via the main valencies. (that is to say substituents bonded by covalent bonds), such as hetero-atoms, especially halogen atoms, such as chlorine atoms or carbonyl groups. Platinum metal complexes of this nature which a take up carbon monoxide are able to take up carbon monoxide via main valencies, that is to say by covalent bonds.

Platinum metal complexes used are, for example, platinum metal complexes containing phosphorus, above all phosphine-platinum metal complexes which contain one, two or more phosphines. These phosphines preferably contain, as substituents, optionally substituted aliphatic, cycloaliphatic, aromatic or araliphatic hydrocarbon radicals, above all lower alkyl, for example n-butyl, or especially optionally substituted phenyl, such as phenyl, as subsituents. Apart from the parts containing phosphorus, for example the phosphines, the platinum metal complexes can contain further organic ligands especially those which can replace one, two or more phosphorus-containing ligands, such as phosphines, in an existing phosphorus-containing platinum metal complex, for example suitable nitriles, such as acetonitrile, bonded by non-covalent bonds to the metal atom, and/or halogen atoms, for example chlorine, or carbonyl groups bonded by covalent bonds to the metal atom.

Preferably, bis-trisubstituted phosphine-platinum halides, bis-trisubstituted phosphine-carbonyl-iridium halides or tris-trisubstituted phosphine-iridium halides are used, but above all tris-trisubstituted phosphine-rhodium halides, wherein the substituents of the phosphine preferably represent lower alkyl, for example n-butyl, and above all phenyl, and the halides are above all chlorides. Such phosphine-platinum metal complexes which are capable of taking up carbon monoxide bonded by covalent bonds are, for example, bis-triphenylphosphine-platinum-II chloride [(C₆H₅)₃P]₂PtCl₂ or bis-triphenylphosphine-carbonyliridium-II chloride [(C₆H₅)₃P]₂ Ir(CO)Cl, as well as tris-triphenylphosphine-iridium-I chloride [(C₆H₅)₃P]₃ IrCl, but above all tris-triphenyl-phosphine-rhodium-I chloride [(C₆H₅)₃P]₃RhCl.

If desired or required, the decarbonylation with the abovementioned heavy metal complexes can be carried out in the presence of suitable catalysts or activators, for example Lewis acid, such as boron trifluoride (which can be used, for example, together with the bis-triphenylphosphine-platinum chloride), or of a perchlorate, such as an alkali metal perchlorate, for example sodium perchlorate (which can be used, for example, together with bistriphenylphosphine-carbonyliridium chloride).

The reaction is preferably carried out in the presence of inert solvents, especially of hydrocarbons, such as aliphatic or cycloaliphatic but especially aromatic hydrocarbons, for example benzene, toluene or xylene, halogenated hydrocarbons, such as appropriate aliphatic or aromatic chlorinated hydrocarbons, for example methylene chloride or chlorobenzene, ethers, such as aliphatic, cycloaliphatic or aromatic ethers as well as mixed ethers, for example di-n-butyl ether, dioxane, diphenyl ether or anisole, nitriles, such as aliphatic or aromatic nitriles, for example acetonitrile or benzonitrile, or ketones, especially aliphatic ketones, such as lower alkanones, for example acetone, ethyl methyl ketone or isobutyl methyl ketone, or mixtures of such solvents. The reaction is carried out with cooling, at room temperature or with warming, for example at about 10° C. to about 150° C., such as at about 40° C. to about 120° C. and also, if necessary, in a closed vessel and/or in an inert gas atmosphere, for example under nitrogen or argon.

In the process according to the invention, if necessary, free functional groups which are present in the starting substances and do not participate in the reaction can be transiently protected in a manner which is in itself known, for example free hydroxyl, mercapto and amino groups by, for example, acylation, tritylation or silylation and free carboxyl groups by, for example, esterification, including silylation, and can in each case, if desired, be liberated in a manner which is in itself known after the reaction has taken place.

The resulting compounds of the formula I can be converted into one another in a manner which is in itself known.

In a resulting compound it is possible, for example, for an amino group $R_1^A$ or $R_1^b$, especially an acyl group which can easily be split off, to be split off in a manner which is in itself known, a tert.-butoxycarbonyl group for example, by treatment with trifluoroacetic acid and a 2,2,2-trichloroethoxycarbonyl, 2-iodoethoxycarbonyl or phenacyloxycarbonyl group by treatment with a suitable metal or a metal compound, for example zinc, or a chromium-II compound, such as chromium-II chloride or chromium-II acetate, advantageously in the presence of a hydrogen-releasing agent which together with the metal or the metal compound generates nascent hydrogen, preferably in the presence of acetic acid containing water. It is furthermore possible, in a resulting compound of the formula I wherein a carboxyl group —C(=O)—O—R$_2$ preferably represents a carboxyl group which is protected, for example, by esterification, including silylation or stannylation, for example by reaction with a suitable organic halogenosilicon or halogeno-tin-IV compound, such as trimethylchlorosilane or tri-n-butyl-tin chloride, to split off a suitable acyl group $R_1^A$ or $R_1^b$, wherein free functional groups which may be present are protected if appropriate, by treatment with an imide-halide-forming agent, reaction of the resulting imide-halide with an alcohol and splitting of the imino-ether formed, it being possible for a protected carboxyl group, for example a carboxyl group protected by an organic silyl radical, to be liberated already in the course of the reaction.

Imide-halide-forming agents in which halogen is bonded to an electrophilic central atom are above all acid halides, such as acid bromides and especially acid colorides. These are above all acid halides of inorganic acids, above all of acids containing phosphorus, such as phosphorus oxyhalides, phosphorus trihalides and especially phosphorus pentahalides, for example phosphorus oxychloride, phosphorus trichloride and above all phosphorus pentachloride, and also pyrocatechyl-phosphorus trichloride, as well as acid halides, especially acid chlorides, of acids containing sulphur or of carboxylic acids, such as thionyl chloride, phosgene or oxalyl chloride.

The reaction with one of the imide-halide forming agents mentioned is preferably carried out in the presence of a suitable base, especially an organic base, above all a tertiary amine, for example a tertiary aliphatic monoamine or diamine, such as tri-lower alkylamine, for example trimethylamine, triethylamine or ethyl diisopropylamine, and also of an N,N,N',N'-tetra-lower alkyl-lower alkylenediamine, for example N,N,N',N'-tetramethyl-1,5-pentylenediamine or N,N,N',N'-tetramethyl-1,6-hexyldiamine, a monocyclic or bicyclic monoamine or diamine, such as a N-substituted, for example N-lower alkylated, alkyleneamine, azaalkyleneamine or oxaalkyleneamine, for example N-methyl-piperidine or N-methyl-morpholine, or 2,3,4,6,7,8-hexahydro-pyrolo[1,2-a]pyrimidine (diazabicyclononenes; DBN) or a tertiary aromatic amine, such as a di-lower alkyl-aniline, for example N,N-dimethylaniline, or above all a tertiary heterocyclic, monocyclic or bicyclic base, such as quinoline or isoquinoline, especially pyridine, preferably in the presence of a solvent, such as an optionally halogenated, for example chlorinated, aliphatic or aromatic hydrocarbon, for example methylene chloride. Approximately equimolar amounts of the imide-halide-forming agent and of the base can be used; the latter can however also be present in excess or in less than equimolar amount, for example in about 0.2-fold to about 1-fold amount, or in up to about 10-fold excess, especially about 3-fold to 5-fold excess.

The reaction with the imide-halide-forming agent is preferably carried out with cooling, for example at temperatures of about −50° C. to about +10° C., but higher temperatures, that is to say, for example, up to about 75° C., can also be used if the stability of the starting substances and products permits a higher temperature.

The imide-halide product which is usually further processed without isolation, is reacted, according to the process, with an alcohol, preferably in the presence of one of the abovementioned bases, to give the imino-ether. Suitable alcohols are, for example, aliphatic as well as araliphatic alcohols, above all optionally substituted, such as halogenated, for example chlorinated lower alkanols, or alkanols possessing additional hydroxyl groups, for example ethanol, n-propanol, isopropanol or n-butanol, especially methanol, and also 2,2,2-trichloroethanol, as well as optionally substituted phenyl-lower alkanols, such as benzyl alcohol. Usually an excess, for example up to an about 100-fold excess, of the alcohol is used and the reaction is preferably carried out with cooling, for example at temperatures of about −50° C. to about 10° C.

The imino-ether product can advantageously be subjected to splitting without isolation. The splitting of the imino-ether can be achieved by treatment with a suitable hydroxy compound. For this, water, or an aqueous mixture of an organic solvent, such as an alcohol, especially a lower alkanol, for example methanol, is preferably used. The process is usually carried out in an acid medium, for example at a pH-value of about 1 to about 2 which can, if necessary, be adjusted by adding a basic agent, such as an aqueous alkali metal hydroxide, for example sodium hydroxide or potassium hydroxide, or an acid, for example a mineral acid or an organic acid, such as hydrochloric acid, sulphuric acid, phosphoric acid, fluoboric acid, trifluoroacetic acid or p-toluenesulphonic acid.

The three-stage process described above for splitting off an acyl group is advantageously carried out without isolation of the imide-halide and imino-ether intermediate products, usually in the presence of an organic solvent which is inert towards the reactants, such as an optionally halogenated hydrocarbon, for example methylene chloride, and/or in an inert gas atmosphere, such as a nitrogen atmosphere.

If the imide-halide intermediate product obtainable in accordance with the above process, instead of being reacted with an alcohol, is reacted with a salt, such as an alkali metal salt, of a carboxylic acid, especially a sterically hindered carboxylic acid, a compound of the formula I wherein both radicals $R_1^a$ and $R_1^b$ represent acyl groups, is obtained.

In a compound of the formula I wherein both radicals $R_1^a$ and $R_1^b$ represent acyl groups, one of these groups, preferably the sterically less hindered group, can be removed selectively, for example by hydrolysis or aminolysis.

In a compound of the formula I wherein $R_1^A$ and $R_1^b$ together with the nitrogen atom represent a phthalimido group, the latter can be converted into the free amino group by, for example, hydrazinolysis, that is to say on treatment of such a compound with hydrazine.

Certain acyl radicals $R_1^A$ of an acylamino grouping in compounds obtainable according to the invention, such as, for example, the 5-amino-5-carboxy-valeryl radical, wherein the carboxyl group and/or the amino group are optionally protected, can also be split off by treatment with a nitrosylating agent, such as nitrosyl chloride, with a carbocyclic arenediazonium salt, such as benzenediazonium chloride, or with an agent which releases positive halogen, such as a N-halogeno-amine or -imide, for example N-bromosuccinimide, preferably in a suitable solvent or solvent mixture, such as formic acid together with a nitro- or cyano-lower alkane; and treatment of the reaction product with a hydroxylic agent, such as water or a lower alkanol, for example methanol, or, if in the 5-amino-5-carboxy-valeryl radical $R_1^A$ the amino group is unsubstituted and the carboxyl group is protected, for example by esterification, and $R_1^b$ preferably represents an acyl radical but can also denote hydrogen, by allowing the compound to stand in an inert solvent, such as dioxane or a halogenated aliphatic hydrocarbon, for example methylene chloride and, if necessary, working-up the free or mono-acylated amino compound in accordance with methods which are in themselves known.

A formyl group $R_1^A$ can also be split off by treatment with an acid agent, for example p-toluenesulphonic acid or hydrochloric acid, a weakly basic agent, for example dilute ammonia, or a decarbonylating agent, for example tris-(triphenylphosphine)-rhodium chloride.

A triarylmethyl group, such as the trityl group $R_1^A$, can be split off, for example, by treatment with an acid agent, such as a mineral acid, for example hydrochloric acid.

In a compound of the formula I, wherein $R_1^a$ and $R_1^b$ represent hydrogen, the free amino group can be acylated in accordance with acylation methods which are in themselves known, for example by treatment with carboxylic acids or reactive acid derivatives thereof, such as halides, for example fluorides or chlorides, or anhydrides (by which there are also to be understood the internal anhydrides of carboxylic acids, that is to say ketenes, or of carbamic or thiocarbamic acids, that is to say isocyanates or isothiocyanates or mixed anhydrides, such as those which can be formed, for example, with chloroformic acid lower alkyl esters, such as ethyl esters, or trichloroacetic acid chloride), or activated esters, as well as with substituted formimino derivatives, such as substituted N,N-dimethylchloroformimino derivatives, or a N-substituted N,N-diacylamine, such as a N,N-diacylated aniline, the reaction being carried out, if necessary, in the presence of suitable condensation agents, when using acids, for example, in the presence of carbodiimides such as dicyclohexylcarbodiimide, and when using reactive acid derivatives, for example, in the presence of basic agents, such as triethylamine or pyridine, it also being possible, if appropriate, to start from salts, for example ammonium salts of compounds of the formula I, wherein $R_2$ represents hydrogen.

An acyl group can also be introduced if a compound of the formula I, wherein $R_1^a$ and $R_1^b$ represent hydrogen, is reacted with an aldehyde such as aliphatic, aromatic or araliphatic aldehyde, and the resulting Schiff's base is acylated, for example in accordance with the methods indicated above, and the acylation product is hydrolysed, preferably in a neutral or weakly acid medium.

An acyl group can also be introduced stepwise. Thus it is possible, for example, to introduce into a compound of the formula I having a free amino group, a halogeno-lower alkanoyl group, for example a bromoacetyl group or, for example, by treatment with a carbonic acid dihalide, such as phosgene, a halogenocarbonyl group, for example chlorocarbonyl group, and to react a N-(halogeno-lower alkanoyl)-or N-(halogenocarbonyl)-amino compound thus obtainable with suitable exchange reagents, such as basic compounds, for example tetrazole, thio compounds, for example 2-mercapto-1-methyl-imidazole, or metal salts, for example sodium azide, or alcohols, such as lower alkanols, for example tert.-butanol, and thus to obtain substituted N-lower alkanoylamino or N-hydroxycarbonylamino compounds. It is furthermore possible, for example, to react a compound of the formula I wherein $R_1^a$ represents a glycyl group which is preferably substituted in the α-position, such as phenylglycyl, and $R_1^b$ represents hydrogen, with an aldehyde, for example formaldehyde, or a ketone, such as a lower alkanone, for example acetone, and thus to obtain compounds of the formula I, wherein $R_1^A$ and $R_1^b$ together represent a 5-oxo-1,3-diaza-cyclopentyl radical which is preferably substituted in the 4-position and is optionally substituted in the 2-position.

In both reactants, free functional groups can, during the acylation reaction, be transiently protected in a manner which is in itself known, and be liberated, after the acylation, by means of methods which are in themselves known. Thus it is preferentially possible, for example, to protect amino or carboxyl groups in the acyl radical during the acylation reaction, for example in the form of acylamino groups, such as 2,2,2-trichloroethoxycarbonylamino, 2-bromoethoxycarbonylamino or tert.-butoxycarbonylamino groups, or in the form of esterified carboxyl groups, such as diphenylmethoxycarbonyl groups, and subsequently, optionally after conversion of the protective group, for example of a 2-bromoethoxycarbonyl group into a 2-iodoethoxycarbonyl group, to split such protected groups, for example by treatment with suitable reducing agents, such as zinc in the presence of aqueous acetic acid, or with trifluoroacetic acid, or by hydrogenolysis.

The acylation can also be effected by replacement of an already existing acyl group by another, preferably sterically hindered, acyl group, for example in accordance with the process described above, by manufacturing the imide-halide compound, treating this with a salt of an acid and hydrolytically splitting off one of the acyl groups present in the product thus obtainable, usually the sterically less hindered acyl group.

In a compound of the formula I, wherein $R_1^a$ and $R_1^b$ represent hydrogen, the free amino group can also be protected by introducing a triarylmethyl group, for example by treatment with a reactive ester of a triarylmethanol, such as trityl chloride, preferably in the presence of a basic agent, such as pyridine.

An amino group can also be protected by introducing a silyl and stannyl group. Such groups are introduced in a manner which is in itself known, for example by treatment with a suitable silylating agent, such as a dihalogeno-dilower alkyl-silane, or tri-lower alkyl-silyl halide, for example dichloro-dimethylsilane or trimethyl-silyl chloride, or an optionally N-mono-lower alkylated, N,N-di-lower alkylated, N-tri-lower alkylsilylated or N-lower alkyl-N-tri-lower alkylsilylated N-(tri-lower alkyl-silyl)-amine (see, for example, British Pat. No. 1,073,530) or with a suitable stannylating agent, such as a bis-(tri-lower alkyltin)-oxide, for example bis-(tri-n-butyl-tin)-oxide, a trilower alkyl-tin hydroxide, for example triethyl-tin hydroxide, a tri-lower alkyl-lower alkoxy-tin, tetra-lower alkoxy-tin or tetra-lower alkyl-tin compound, or a trilower alkyl-tin halide, for example tri-n-butyl-tin chloride (see, for example, Netherlands Published Specification 67/17,107).

In a compound of the formula I obtainable according to the process, which possesses a group of the formula $-C(=O)-O-R_2$, wherein $R_2$ represents hydrogen, the free carboxyl group can be esterified in a manner which is in itself known to give a protected carboxyl group, for example by treatment with a diazo compound, such as a diazolower alkane, for example diazomethane or diazoethane, or a phenyl-diaza-lower alkane, for example phenyldiazomethane or diphenyldiazomethane, or by reaction with an alcohol suitable for esterification in the presence of an esterifying agent, such as a carbodiimide, for example dicyclohexylcarbodiimide or carbonyldiimidazole, or in accordance with any other known and suitable esterification process, such as reaction of a salt of the acid with a reactive ester of an alcohol and of a strong inorganic acid, as well as of a strong organic sulphonic acid. Furthermore, acid halides, such as acid chlorides (manufactured, for example, by treatment with oxalyl chloride), activated esters (formed, for example, with N-hydroxy-nitrogen compounds) or mixed anhydrides (obtained, for example, with halogenoformic acid lower alkyl esters such as chloroformic acid ethyl ester, or with halogenoacetic acid halides, such as trichloracetic acid chloride) can be converted into an esterified carboxyl group by reaction with alcohols, if appropriate in the presence of a base, such as pyridine.

Mixed anhydrides can be manufactured if a compound of the formula I, wherein $R_2$ represents hydrogen, and preferably a salt thereof, especially an alkali metal salt or ammonium salt thereof, is reacted with a reactive derivative, such as a halide, for example the chloride, of an acid, for example a halogenoformic acid lower alkyl ester or a lower alkanecarboxylic acid chloride.

In a resulting compound, a grouping of the formula $-C(=O)-O-R_2^A$ can be converted into another grouping of this formula, for example 2-chloroethoxycarbonyl or 2-bromoethoxycarbonyl of the formula $-C(=O)-O-R_2^a$ can be converted into 2-iodoethoxycarbonyl by treatment with an iodine salt, such as sodium iodide, in the presence of a suitable solvent, such as acetone.

Carboxyl groups protected by organic silyl or stannyl groups can be formed in a manner which is in itself known, for example if compounds of the formula I, wherein $R_2$ represents hydrogen, or salts, such as alkali metal salts, for example sodium salts, thereof are treated with suitable silylating or stannylating agent, such as one of the abovementioned silylating or stannylating agents; see, for example, British Pat. No. 1,073,530 or Netherlands Published Specification No. 67/17,107.

In a compound of the formula I obtainable according to the invention, having an esterified carboxyl group, wherein the latter for example represents an esterified carboxyl group of the formula $-C(=O)-O-R_2^A$ which can easily be converted into the free carboxyl group, the esterified carboxyl group can be converted into the free carboxyl group in a manner which is in itself known and depends, for example, on the nature of the esterifying radical $R_2^A$, a grouping of the formula $-C(=O)-OR_2^a$ or $-C(=O)-OR_2^b$, for example, by treatment with a chemical reducing agent, such as a metal, for example zinc, or a reducing metal salt, such as a chromium-II salt, for example chromium-II chloride, usually in the presence of a hydrogen-releasing agent which is capable of generating nascent hydrogen together with the metal, such as an acid, above all acetic acid or formic acid, or an alcohol, water being preferably added, a grouping of the formula $-C(=O)-OR_2^b$ also by treatment with a nucleophilic, preferably salt-forming reagent, such as sodium thiophenolate or sodium iodide, a grouping of the formula $-C(=O)-OR_2^c$, for example, by irradiation, preferably with ultraviolet light, using ultraviolet light or shorter wavelengths, for example below 290 mμ, if $R_2^c$ for example represents a benzyl radical which is optionally substituted in the 3-, 4- and/or 5-position, for example by lower alkoxy and/or nitro groups, or using ultraviolet light of longer wavelengths, for example above 290 mμ, if $R_2^c$ denotes, for example, a benzyl radical substituted in the 2-position by a nitro group, a grouping $-C(=O)-OR_2^d$, for example, by treatment with a suitable acid agent, such as formic acid or trifluoroacetic acid, optionally with the addition of a nucleophilic compound, such as phenol or anisole, a grouping $-C(=O)-OR_2^e$ by hydrolysis, for example by treatment with an acid or weakly basic aqueous agent, such as hydrochloric acid or aqueous sodium bicarbonate or an aqueous potassium phosphate buffer of pH about 7 to about 9, and a grouping $-C(=O)-OR_2^f$ by hydrogenolysis, for example by treatment with hydrogen in the presence of a noble metal catalyst, for example a palladium catalyst.

A carboxyl group which is protected, for example by silylation or stannylation, can be liberated in the usual manner, for example by treatment with water or an alcohol.

It is furthermore possible to liberate modified functional groups, such as acylated amino groups or esterified carboxyl groups, in accordance with methods which are in themselves known, for example those described above, or functionally to modify, for example acylate or esterify, or substitute, free functional groups, such as amino or carboxyl groups, in accordance with processes which are in themselves known. Thus, for example, an amino group can be converted into a sulphoamino group by treatment with sulphur trioxide, preferably in the form of a complex with an organic base, such as a tri-lower alkylamine, for example triethylamine. It is furthermore possible to react the reaction mixture of an acid addition salt of a 4-guanylsemicarbazide with sodium nitrite with a compound of the formula I, wherein, for example, the amino protective group $R_1^A$ represents an optionally substituted glycyl group, and thus to convert the amino group into a 3-guanylureido group.

It is furthermore possible to convert ceph-2-em compounds obtainable according to the invention into the corresponding ceph-3-em compounds in a manner which is in itself known, and in this it is possible to employ ceph-2-em compounds of the formula I in which the grouping of the formula $-C(=O)-O-R_2$ represents a free or protected carboxyl group, above all an esterified carboxyl group or a carboxyl group present as a mixed anhydride grouping, or wherein such a protected carboxyl group can be formed during the reaction.

Thus it is possible to isomerise ceph-2-em compounds of the formula I by treating them with a weakly basic agent and isolating the corresponding ceph-3-em compound. Suitable isomerising agents are, for example, organic nitrogen-containing bases, especially tertiary heterocyclic bases of aromatic character, above all bases of the pyridine type, such as pyridine itself, as well as collidines or lutidines, and also quinoline, tertiary aromatic bases, for example those of the aniline type, such as N,N-di-lower alkylanilines, for example N,N-dimethylaniline or N,N-diethylaniline, or tertiary aliphatic, azacycloaliphatic or araliphatic bases, such as N,N,N-tri-lower alkylamines, for example N,N,N-trimethylamine, N,N-dimethyl-N-ethylamine, N,N,N-triethylamine or N,N,N-diisopropyl-N-ethylamine, N-lower alkyl-azacycloalkanes, for example N-methylpiperidine, or N-phenyl-lower alkyl-N,N-di-lower alkyl-amines, for example N-benzyl-N,N-dimethylamine, as well as mixtures thereof, such as the mixture of a base of the pyridine type and a N,N,N-tri-lower alkylamine, for example pyridine and triethylamine. It is furthermore also possible to use inorganic or organic salts of bases, especially of mediumstrength to strong bases with weak acids, such as alkali metal salts or ammonium salts of lower alkanecarboxylic acids, for example sodium acetate, triethylammonium acetate or N-methylpiperidine acetate, as well as other analogous bases or mixtures of such basic agents.

The above isomerisation with basic agents can for example be carried out in the presence of a derivative of a carboxylic acid which is suitable for the formation of a mixed anhydride, such as of a carboxylic acid anhydride or carboxylic acid chloride, for example with pyridine in the presence of acetic anhydride. At the same time, an anhydrous medium is preferably used, in the presence or absence of a solvent, such as of an optionally halogenated, for example chlorinated, aliphatic, cycloaliphatic or aromatic hydrocarbon, or of a solvent mixture, with bases used as reactants which are liquid under the reaction conditions being able simultaneously also to serve as solvents, with cooling, at room temperature or with heating, preferably in a temperature range of about $-30°$ C. to about $+100°$ C., in an inert gas atmosphere, for example a nitrogen atmosphere, and/or in a closed vessel.

The ceph-3-em compounds thus obtainable can be separated from ceph-2-em compounds which may still be present, in a manner which is in itself known, for example by adsorption and/or crystallisation.

The isomerisation of ceph-2-em compounds of the formula I can also be carried out if these compounds are oxidised in the 1-position, an isomer mixture of the 1-oxides which is obtainable is separated if desired, and the 1-oxides of the corresponding ceph-3-em compounds, thus obtainable, are reduced.

Suitable oxidising agents for the oxidation of ceph-2-em compounds in the 1-position are inorganic peracids which have a reduction potential of at least 30 1.5 volt and consist of non-metallic elements, organic peracids or mixtures of hydrogen peroxide and acids, especially organic carboxylic acids having a dissociation constant of at least $10^{-5}$. Suitable inorganic per-acids are periodic acid and persulphuric acid. Organic per-acids are corresponding percarboxylic and persulphonic acids which can be added as such or can be formed in situ by the use of at least one equivalent of hydrogen peroxide and of a carboxylic acid. It is desirable to use a large excess of the carboxylic acid if, for example, acetic acid is used as the solvent. Suitable per-acids are, for example, performic acid, peracetic acid, trifluoroperacetic acid, permaleic acid, perbenzoic acid, 3-chloroperbenzoic acid, monoperphthalic acid or p-toluenepersulphonic acid.

The oxidation can also be carried out using hydrogen peroxide with catalytic amounts of an acid having a dissociation constant of at least $10^{-5}$. It being possible to employ low concentrations, for example 1–2% and below, but also larger amounts of the acid. The activity of the mixture above all depends on the strength of the acid. Suitable mixtures are, for example, mixtures of hydrogen peroxide with acetic acid, perchloric acid or trifluoroacetic acid.

The above oxidation can be carried out in the presence of suitable catalysts. Thus, for example, the oxidation with percarboxylic acids can be catalysed by the presence of an acid having a dissociation constant of at least $10^{-5}$, its activity depending on its strength. Acids suitable for use as catalysts are, for example, acetic acid, perchloric acid and trifluoroacetic acid. Usually, at least equimolar amounts of the oxidising agent, preferably a slight excess of about 10% to about 20%, are used, but larger excesses, that is to say up to the 10-fold amount of the oxidising agent or above, can also be used. The oxidation is carried out under mild conditions, for example at temperatures of about $-50°$ C. to about $+100°$ C., preferably about $-10°$ C. to about $+40°$ C.

In the 1-oxides of ceph-3-em compounds of the formula I, thus obtainable, especially in those compounds in which $R_1^a$, $R_1^b$ and $R_2$ have the abovementioned preferred meanings, the groups $R_1^a$, $R_1^b$ and/or $R_2$ can, within the set framework, be converted into one another, split off or introduced. A mixture of isomeric α- and β-1-oxides can be separated by, for example, chromatography.

The reduction of the 1-oxides of ceph-3-em compounds of the formula I can be carried out in a manner which is in itself known, by treatment with a reducing agent, if necessary in the presence of an activating agent. Possible reducing agents are: catalytically activated hydrogen, using noble metal catalysts which contain palladium, platinum or rhodium, and which are optionally used together with a suitable carrier material, such as charcoal or barium sulphate; reducing tin, iron, copper or manganese cations, which are used in the form of appropriate compounds or complexes of inorganic or organic nature, for example as tin-II chloride, fluoride, acetate or formate, iron-II chloride, sulphate, oxalate or succinate, copper-I chloride, benzoate or oxide, or manganese-II chloride, sulphate, acetate or oxide, or as complexes, for example with ethylenediaminetetraacetic acid or nitriloacetic acid; reducing dithionite, iodide or ferrocyanide anions, which are used in the form of appropriate inorganic or organic salts, such as alkali metal dithionite, for example sodium dithionite or potassium dithionite, sodium iodide or potassium iodide or sodium ferrocyanide or potassium ferrocyanide, or in the form of the corresponding acids, such as hydriodic acid; reducing trivalent inorganic or organic phosphorus compounds, such as phosphines and also esters, amides and halides of phosphinous, phosphonous and phosphorous acid, as well as phosphorussulphur compounds corresponding to these phosphorus-oxygen compounds, with organic radicals above all representing aliphatic, aromatic or araliphatic radicals, for example optionally substituted lower alkyl, phenyl or phenyl-lower alkyl groups, such as, for example, triphenylphosphine, tri-n-butylphosphine, diphenylphosphine acid methyl ester, diphenylchlorophosphine, phenyldichlorophosphine, benzenephosphonous acid dimethyl ester, butanephosphonous acid methyl ester, phosphorous acid triphenyl ester, phosphorous acid trimethyl ester, phosphorus trichloride, phosphorus tribromide and the like; reducing halogenosilane compounds which possess at least one hydrogen atom bonded to the silicon atom and which apart from halogen, such as chlorine, bromine or iodine, can also contain organic radicals, such as aliphatic or aromatic groups, for example optionally substituted lower alkyl or phenyl groups, such as chlorosilane, bromosilane, dichlorosilane or trichlorosilane, dibromosilane or tribromosilane, diphenylchlorosilane, dimethylchlorosilane and the like; reducing quaternary chloromethylene-iminium salts, especially chlorides or bromides, wherein the iminium group is substituted by a bivalent or two monovalent organic radicals, such as optionally substituted lower alkylene or lower alkyl groups, such as N-chloromethylene-N,N-diethyliminium chloride or N-chloromethylene-pyrrolidiniminium chloride; and complex metal hydrides, such as sodium borohydride, in the presence of suitable activating agents, such as cobalt-II chloride.

Activating agents which are used together with those of the abovementioned reducing agents which do not themselves display Lewis acid properties, that is to say which are above all employed together with the dithionite, iodide or ferrocyanide reducing agents and the trivalent phosphorus reducing agents which do not contain halogen, or in the catalytic reduction, are especially organic carboxylic acid halides and sulphonic acid halides and also sulphur, phosphorus or silicon halides having a second order hydrolysis constant equal to, or higher than, that of benzoyl chloride, for example phosgene, oxalyl chloride, acetic acid chloride or bromide, chloroacetic acid chloride, pivalic acid chloride, 4-methoxybenzoic acid chloride, 4-cyanobenzoic acid chloride, p-toluenesulphonic acid chloride, methanesulphonic acid chloride, thionyl chloride, phosphorus oxychloride, phosphorus trichloride, phosphorus tribromide, phenyldichlorophosphine, benzenephosphonous acid dichloride, dimethylchlorosilane or trichlorosilane and also suitable acid anhydrides, such as trifluoroacetic anhydride or cyclic sultones, such as ethanesultone, 1,3-propanesultone, 1,4-butanesultone or 1,3-hexanesultone.

The reduction is preferably carried out in the presence of solvents or mixtures thereof, the choice of which is above all determined by the solubility of the starting substances and the choice of the reducing agents, such as, for example, lower alkanecarboxylic acids or esters thereof, such as acetic acid and ethyl acetate in the case of the catalytic reduction and, for example, optionally substituted, such as halogenated or nitrated, aliphatic, cycloaliphatic, aromatic or araliphatic hydrocarbons, for example benzene, methylene chloride, chloroform or nitromethane, suitable acid derivatives, such as lower alkanecarboxylic acid esters or nitriles, for example ethyl acetate or acetonitrile, or amides of inorganic or organic acids, for example dimethylformamide or hexamethylphosphoramide, ethers, for example diethyl ether, tetrahydrofurane or dioxane, ketones, for example acetone, or sulphones, especially aliphatic sulphones, for example dimethylsulphone or tetramethylenesulphone and the like, in conjunction with the chemical reducing agents, these solvents preferably being anhydrous. The reaction is usually carried out at temperatures of about $-20°$ C. to about $100°$ C., and when using very reactive activating agents the reaction can be carried out at lower temperatures.

Salts of compounds of the formula I can be manufactured in a manner which is in itself known. Thus, for example, salts of compounds of the formula I, wherein $R_2$ represents hydrogen, can for example be formed by treatment with metal compounds, such as alkali metal salts of suitable carboxylic acids, for example the sodium salt of α-ethylcaproic acid, or with ammonia or a suitable organic amine, using, preferably, stoichiometric amounts or only a slight excess of the salt-forming agent. Acid addition salts of compounds of the formula I with basic groupings are obtained in the usual manner, for example by treatment with an acid or with a suitable anion exchange reagent. Internal salts of compounds of the formula I which contain a salt-forming amino group and a free carboxyl group, can be formed, for example, by neutralisation of salts, such as acid addition salts, to the iso-electric point, for example with weak bases, or by treatment with liquid ion exchangers.

Salts can be converted into the free compounds in the usual manner, metal salts and ammonium salts, for example, by treatment with suitable acids, and acid addition salts, for example, by treatment with a suitable basic agent.

Resulting mixtures of isomers can be separated into the individual isomers in accordance with methods which are in themselves known, for example by fractional crystallisation, adsorption chromatography (column chromatography or thin layer chromatography) or other suitable methods of separation. Resulting racemates can be separated into the antipodes in the usual manner, if appropriate after introduction of suitable salt-forming groupings, for example by forming a mixture of diastereoisomeric salts with optically active salt-forming agents, separating the mixture into the diastereoisomeric salts and converting the separated salts into the free compounds, or by fractional crystallisation from optically active solvents.

The process also encompasses those embodiments according to which compounds which arise as intermediate products are used as starting substances and the remaining process steps are carried out with these, or the process is stopped at any stage; furthermore, starting substances can be used in the form of derivatives or can be formed during the reaction.

Preferably, such starting substances are used, and the reaction conditions are so chosen, that the compounds listed initially as being particularly preferred are obtained.

An additional subject of the present invention are the 1-oxides of the compounds of the formula I, in which the double bond is in the 3,4-position and in which $R_1{}^a$, $R_1{}^b$ and $R_2$ have the previously given, particularly the preferred meaning, as well as salts of such compounds having salt-forming groups.

A further subject of the present invention are the ceph-2-em compounds of the formula

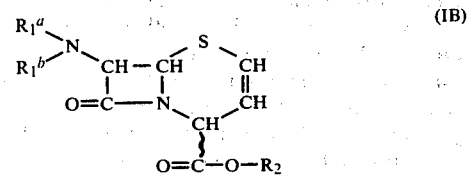

(IB)

wherein $R_1{}^a$, $R_1{}^b$ and $R_2$ have the abovementioned meanings, especially the preferred meanings, and above all those compounds of the formula Ib, wherein $R_1{}^b$ represents hydrogen, $R_1{}^a$ represents hydrogen or an acyl radical of the formula Ia, wherein Ar and R have the abovementioned meanings, or wherein $R_1{}^a$ denotes the acyl group of the formula Ia, in which Ar has the above meaning, and R represents an amino group which is joined to $R_1{}^b$, which represents methylene or isopropylidene, and $R_2$ represents hydrogen, tert.-butyl, 2,2,2-trichloroethyl, 2-iodoethyl, 2-bromoethyl, phenacyl, 4-nitrobenzyl or 4-methoxybenzyl, and also diphenylmethyl, 4,4'-dimethoxydiphenylmethyl, trityl or bis-(4-methoxyphenyloxy)-methyl, or salts of such compounds having salt-forming groups.

The starting substances of the formula II used according to the invention are known or can be manufactured in a manner which is in itself known. Thus, for example, the starting substances of the formula II can be obtained in accordance with the process described in Netherlands Published Specification No. 68.15,631, for example if in a ceph-2-em or ceph-3-em compound of the formula

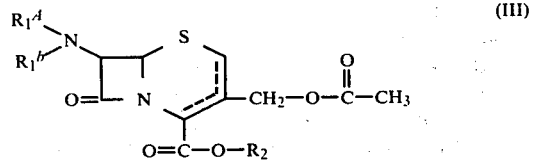

(III)

wherein $R_2$ preferably represents hydrogen, the acetoxymethyl group is converted into the hydroxymethyl group, for example by hydrolysis in a weakly basic medium, such as with an aqueous sodium hydroxide solution at pH 9-10, or by treatment with a suitable esterase, such as an appropriate enzyme from *Rhizobium tritolii, Rhizobium lupinii, Rhizobium japonicum* or *Bacterium subtilis*, the hydroxymethyl group is oxidised to a formyl group and, if desired or required, in a resulting compound a hydrogen atom $R_2$ is replaced by a suitable organic radical. The oxidation can for example be carried out in accordance with the process described in U.S.A. Pat. No. 3,351,596, that is to say by treatment with oxidising metal compounds, such as oxides, for example chromium trioxide or manganese dioxide, also with 2,3-dichloro-5,6-dicyano-1,4-benzoquinone, or advantageously by treatment with aliphatic sulphoxides, such as di-lower alkylsulphoxides, for example dimethylsulphoxide, or lower alkylenesulphoxides, for example tetramethylenesulphoxide, in the presence of aliphatic carboxylic acid anhydrides, for example acetic anhydride, perferably using an excess of the sulphoxide and, compared with the sulphoxide, an equimolar amount of the anhydride, at temperatures of about −50° C. to to about +70° C., if desired in the presence of an additional inert solvent, such as benzene or toluene.

The ceph-2-em starting substances of the formula II can also be obtained by total synthesis, that is to say in accordance with the method described in Austrian Pat. Nos. 263,768 and 264,537.

The heavy metal complexes which take up carbon monoxide which are to be employed in the reaction according to the invention can be manufactured in a manner which is in itself known, for example if the corresponding heavy metal halides, such as rhodium chloride or iridium chloride, optionally in the form of hydrates, are reacted with a phosphine, such as triphenylphosphine, preferably with an excess of a phosphine, in the presence of a suitable solvent, such as a lower alkanol, for example ethanol, preferably at elevated temperature; usually, the desired complex can be obtained in a crystalline form.

The invention is described in the examples which follow.

EXAMPLE 1

A solution of 1.088 g of 3-formyl-7β-phenylacetylamino-ceph-3-em-4-carboxylic acid diphenyl methyl ester in 150 ml of absolute benzene, prepared with warming, is treated with 2.0 g of tris-triphenylphosphine-rhodium-I chloride; the golden yellow solution turns brown and is stirred for one hour at 75°-80° C. The mixture is left to stand for 16 hours and is filtered, and the filtrate is evaporated under reduced pressure. The residue is taken up in a small amount of methylene chloride; the needle-shaped yellow crystal precipitate is filtered off and the filtrate is concentrated and chromatographed on 150 g of silica gel (deactivated with 5% of water and suspended in a 1:1 mixture of toluene and methylene chloride). Non-polar by-products, inter alia triphenylphosphine, are eluted with the 1:1 mixture of toluene and methylene chloride, and the 7β-phenylacetylamino-ceph-3-em-4-carboxylic acid diphenylmethyl ester is eluted with methylene chloride. The slightly brownish, foam-like material is crystallised from a mixture of methylene chloride and diethyl ether, diluted with cyclohexane, and is obtained in the form of almost colourless, felted needles which after two recrystallisations from the same solvent mixture and after drying for 18 hours at 35° C. in a high vacuum melt at 163.5°-164.5° C.; $[\alpha]_D{}^{20} = +30° \pm 1°$ (c=0.968 in dioxane); thin layer chromatogram (silica gel; indentification in ultraviolet light and with iodine vapour): Rf=0.55 (system: toluene/acetone, 4:1), Rf=0.35 (system: toluene/acetone, 9:1) and Rf=0.40 (system:

toluene/ethyl acetate, 4:1); ultraviolet absorption spectrum: $\lambda_{max}=258$ m$\mu$ ($\epsilon=6,100$) and $\lambda_{min}=240$ m$\mu$ ($\epsilon=5,250$) (in methylene chloride) and $\lambda_{max}=259$ m$\mu$ ($\epsilon=6,050$) and $\lambda_{min}=239$ m$\mu$ ($\epsilon=4,950$) (in 95% strength aqueous ethanol); infra-red absorption spectrum: characteristic bands at 2.90$\mu$, 5.57$\mu$, 5.76$\mu$, 5.91$\mu$, 6.09$\mu$, 6.66$\mu$, 7.13$\mu$, 8.12$\mu$, 8.63$\mu$, 9.07$\mu$, 10.43$\mu$ and 12.22$\mu$ (in methylene chloride) and 3.01$\mu$, 5.60$\mu$, 5.82$\mu$, 6.04$\mu$, 6.08$\mu$ (shoulder), 6.15$\mu$ and 7.13$\mu$ (in mineral oil).

The starting material can be manufactured as follows: a solution of 11.82 g of the crude sodium salt of 3-hydroxymethyl-7$\beta$-phenylacetylamino-ceph-3-em-4-carboxylic acid (manufactured by enzymatic desacetylation of the sodium salt of 3-acetoxymethyl-7$\beta$-phenylacetylamino-ceph-3-em4-carboxylic acid by means of a purified enzyme extract from Bacterium subtilis, strain ATCC 6,633, and subsequent lyophilisation of the reaction solution) in 200 ml of water is covered with 400 ml of ethyl acetate and acidified to pH 2 with 20% strength aqueous phosphoric acid. The aqueous phase is separated off and twice re-extracted with 150 ml of ethyl acetate at a time. The organic extracts are washed four times with 50 ml of water at a time, dried over magnesium sulphate and combined, and are then concentrated to about 400 ml. The concentrate is treated with an excess of a diphenyldiazomethane solution in diethyl ether, the mixture is left to stand for 3 hours at room temperature and the granular crystals which have precipitated are then filtered off. The filtrate is concentrated to about 200 ml and is treated with cyclohexane whilst warm, and after cooling to room temperature the mixture is left to stand at 4° C. The 3-hydroxymethyl-7$\beta$-phenylacetylamino-ceph-3-em-4-carboxylic acid diphenylmethyl ester obtainable as a precipitate is filtered off, washed and dried; after recrystallisation from a mixture of acetone and cyclohexane the product melts at 176°–176.5° C. (uncorrected); $[\alpha]_D^{20}=-6°\pm1°$ (c=1.231 in chloroform); thin layer chromatogram (silica gel; detection with iodine vapour or ultraviolet light at 254 m$\mu$): Rf=0.27 (system: chloroform/acetone, 4:1); Rf=0.20 (system: toluene/acetone, 3:1); and Rf=0.53 (system: methylene chloride/acetone, 6:1).

A solution of 0.2 g of 4-hydroxymethyl-7$\beta$-phenylacetylamino-ceph-3-em-4-carboxylic acid diphenylmethyl ester in 5 ml of absolute dimethylsulphoxide and 5 ml of acetic anhydride is left to stand for 5 hours in the dark at room temperature. The greenish-brown reaction solution is evaporated to dryness in a high vacuum, the residue is treated with toluene and the solution is again evaporated to dryness. The crude product is taken up in methylene chloride and the solution is washed with a saturated aqueous sodium chloride solution. The organic phase is dried over magnesium sulphate and the solution is evaporated under reduced pressure. The residue is chromatographed on a column of 10 g of silica gel (addition of 5% of water). The 3-formyl-7$\beta$-phenylacetylamino-ceph-3-em-4-carboxylic acid diphenylmethyl ester is eluted with methylene chloride. The fractions, which are a single substance according to a thin layer chromatogram are dissolved in methylene chloride and cyclohexane is added whilst warm, whereupon a jelly-like precipitate forms. This is filtered off, washed with diethyl ether and pentane and dried on the filter. The light yellow powder thus obtained melts at 123°–125° C. (uncorrected). For analysis, the product is dried in a high vacuum for 20 hours at room temperature; according to the nuclear resonance spectrum, it still contains approx. 1/5 mol of cyclohexane; infra-red spectrum: characteristic bands at 2.90$\mu$, 3.39$\mu$, 5.54$\mu$, 5.77$\mu$, 5.91$\mu$ (shoulder), 5.97$\mu$, 6.22$\mu$, 6.68$\mu$, 7.28$\mu$ and 8.16$\mu$ (in methylene chloride) and at 3.02$\mu$, 5.54$\mu$, 5.77$\mu$, 5.89$\mu$, 6.02$\mu$, 6.23$\mu$, 6.50$\mu$ and 8.02$\mu$; ultraviolet absorption spectrum (in 95% strength ethanol)$_{max}$=310 m$\mu$ ($\epsilon$=9,250) and $\lambda_{min}$=255 m$\mu$ ($\epsilon$=4,950); thin layer chromatogram (silica gel; development with iodine vapour or detection with ultraviolet light at 254m$\mu$): Rf=0.72 (system: ethyl acetate/toluene, 1:1).

EXAMPLE 2:

A solution of 1.05 g of 3-formyl-7$\beta$-phenylacetylamino-ceph-2-em-4$\alpha$-carboxylic acid diphenylmethyl ester in 250 ml of absolute degassed benzene is treated with 1.87 g of tris-triphenylphosphine-rhodium chloride under argon. After warming to 70° C. for two hours and at the reflux temperature for 5$\frac{1}{2}$ hours, the reaction solution is left to stand for 16 hours. A fine precipitate is filtered off; the filtrate is gassed with carbon monoxide and evaporated to dryness, and the residue is taken up in a little methylene chloride. After standing for 20 minutes at 4° C., the lemon yellow precipitate, containing bis-triphenylphosphine-carbonyl-rhodium chloride, is filtered off, washed with pentane and dried. The mother liquors are evaporated to dryness under reduced pressure and chromatographed on 75 g of silica gel. The amorphous 7$\beta$-phenylacetylamino-ceph-2-em-4$\alpha$-carboxylic acid diphenylmethyl ester, which is pure according to a thin layer chromatogram, is eluted with a 4:1 mixture of toluene and methylene chloride; unchanged starting material is eluted with a 3:7 mixture of toluene and methylene chloride.

The analytical product of the 7$\beta$-phenylacetylamino-ceph-2-em-4$\alpha$-carboxylic acid diphenylmethyl ester is again purified by means of chromatography on silica gel, lyophilised from dioxane and dried for 30 hours in a high vacuum at room temperature; thin layer chromatogram (plates; development with iodine vapour; identification with ultraviolet light at $\lambda$254 m$\mu$): Rf=0.53 (system: toluene/acetone, 4:1), Rf=0.75 (system: toluene/acetone, 2:1), Rf=0.73 (system: toluene/ethyl acetate, 1:1), Rf=0.56 (system: toluene/ethyl acetate, 2:1) and Rf=0.36 (system: toluene/ethyl acetate, 4:1); ultraviolet absorption spectrum ($\lambda_{max}$=248 m$\mu$ ($\epsilon$=5,200) and $\lambda_{min}$=242 m$\mu$ ($\epsilon$=5,050) (in 95% strength aqueous ethanol) and $\lambda_{max}$=247 m$\mu$ ($\epsilon$=5,300) and $\lambda_{min}$=243 m$\mu$ ($\epsilon$=5,250) (in methylene chloride); infra-red absorption spectrum (in methylene chloride): characteristic bands at 4.92$\mu$, 5.62$\mu$, 5.72$\mu$, 5.93$\mu$, 6.23$\mu$, 6.64$\mu$, 6.68$\mu$, 6.88$\mu$, 7.16$\mu$, 7.58$\mu$, 8.14$\mu$, 8.35$\mu$, 8.50$\mu$, 8.65$\mu$ and 10.18$\mu$.

The starting material can be manufactured as follows: a suspension of 3.40 g of 3-acetoxymethyl-7$\beta$-phenylacetylamino-ceph-2-em-4$\beta$-carboxylic acid in 70 ml of distilled water is treated with 1 N aqueous sodium hydroxide solution, whilst stirring with a vibro-mixer, until a pH-value of 7.3 is reached. The solution is warmed to 35° C. in a thermostatic bath and is treated with 0.4 g of the cell lyophilisate from Bacillus subtilis ATCC 6,633 in 3 ml of water. The pH-value is kept constant at 7.4 by adding 1 N aqueous sodium hydroxide solution; after about 2$\frac{1}{2}$ hours half the theoretical consumption of sodium hydroxide is reached. The mixture is allowed to complete reacting until no further sodium hydroxide solution is consumed and the pH-value of the reaction solution does not change further even after standing for several hours at room temperature. The solution is covered with 300 ml of cooled ethyl acetate and is acidified to pH 2.0 with 5-molar aqueous phosphoric acid, whilst stirring well. After separating the layers, the aqueous phase is saturated with sodium chloride and extracted with two further portions, each of 250 ml, of cold ethyl acetate. The combined organic phases are washed five times with 50 ml at a time of a saturated aqueous sodium chloride solution, dried over sodium sulphate and evaporated. The residue consists of 3-hydroxymethyl-7β-phenylacetylamino-ceph-2-em-4α-carboxylic acid which chromatographically is a single substance and which after repeated crystallisation in the form of white needle-shaped crystals from a mixture of ethyl acetate and cyclohexane melts at 156°–156.5° C.

A solution of 2.79 g of 3-hydroxymethyl-7β-phenylacetylamino-ceph-2-em-4α-carboxylic acid in 85 ml of absolute dioxane is treated with 2.29 g of 2,3-dichloro-5,6-dicyano-1,4-benzoquinone. The clear reaction mixture is left to stand for 20 hours at 45° C. and is then stored for 2 hours at about 5° C. The 2,3-dichloro-5,6-dicyano-hydroquinone which has precipitated as crystalline platelets is filtered off, the filtrate is evaporated to dryness under reduced pressure, the residue is taken up in a little ethyl acetate and the solution is filtered. The ethyl acetate solution is diluted to 240 ml and whilst being cooled is extracted once with 120 ml and twice with 90 ml at a time of an 0.5 molar aqueous dipotassium hydrogen phosphate solution. The aqueous phases are rinsed with 2 portions of 150 ml of ethyl acetate and are covered with 250 ml of ice-cold ethyl acetate, and the pH-value is adjusted to 2.1 with concentrated phosphoric acid, whilst stirring well. The aqueous phase is separated off, saturated with sodium chloride and extracted with 150 ml and 130 ml of ethyl acetate. The organic extracts are washed four times with 70 ml at a time of a saturated aqueous sodium chloride solution, dried over sodium sulphate and evaporated. An amorphous product is thus obtained which according to a thin layer chromatogram is virtually a single substance, and which is chromatographed on 180 g of silica gel. 3-Formyl-7β-phenylacetylamino-ceph-2-em-4α-carboxylic acid which is pure according to a thin layer chromatogram is eluted with a 4:1 mixture of methylene chloride and ethyl acetate; thin layer chromatogram (silica gel plates): Rf=0.39 (system: n-butanol/acetic acid/water 75:7.5:21). Rf=0.27 (system: n-butanol/ethanol/water, 40:10:50) and Rf=0.53 (system: n-butanol/acetic acid/water, 40:10:40). A further quantity of the pure product can be isolated from the impure fractions by repeated column chromatography. The substance crystallises with inclusion of methanol from a mixture of methanol and methylene chloride, melting point 137.5°–138.5° C.; $[\alpha]_D^{20} = +580 \pm 1°$ (c=1.168% in dioxane); ultraviolet absorption spectrum (in 95% strength ethanol): $\lambda_{max}$=288 mλ ($\epsilon$=18,850) and $\lambda_{min}$=246 mμ ($\epsilon$=2,075).

A solution of 10 g of 3-formyl-7β-phenylacetylamino-ceph-2-em-4α-carboxylic acid in 250 ml of a 4:1 mixture of dioxane and methanol is treated with a solution of 1.5 mol equivalents of diphenyldiazomethane in cyclohexane. After 2 hours at room temperature, the red-violet solution is evaporated to dryness under reduced pressure. The residue is dissolved in hot methylene chloride; the solution is diluted with cyclohexane whilst warm, and 3-formyl-7βphenylacetylamino-ceph-2-em-4α-carboxylic acid diphenylmethyl ester is obtained in practically quantitative yield in the form of fine colourless felted needles, melting point 175.5°–176° C. (uncorrected, decomposition); $[\alpha]_D^{20} = +513° \pm 1°$ (c=1,084 in chloroform); thin layer chromatogram (silica gel): Rf=0.35 (system: toluene/acetone, 80:20) and Rf=0.58 (system: toluene/acetone 65:35); ultraviolet absorption spectrum (in 95% ethanol): $\lambda_{max}$=289 mμ ($\epsilon$=20,200) and $\lambda_{min}$=245 mμ ($\epsilon$=2,100); infrared absorption spectrum: characteristic bands at 2.92μ, 3.53μ, 5.59μ, 5.72μ, 5.91μ, 6.34μ, 6.61μ and 6.67μ (in methylene chloride) and at 3.00μ, 5.63μ, 5.76μ, 5.95μ (double band), 5.99μ, 6.07μ and 6.58μ (in mineral oil).

EXAMPLE 3:

A solution of 1.67 g of 3-formyl-7β-(D-5-diphenylmethoxycarbonyl-5-phthalimido-n-valeroyl-amino)-ceph-3-em-4-carboxylic acid diphenylmethyl ester in 220 ml of absolute degassed benzene is treated with 1.86 g of tris-triphenyl-phosphine-rhodium-I chloride and is warmed under an atmosphere of argon to 70° C. for 2 hours and to the reflux temperature for 6 hours. The mixture is flushed with carbon monoxide and evaporated to dryness, and the residue is taken up in methylene chloride. The yellow bis-triphenylphosphine-carbonyl-rhodium-I chloride is filtered off and the filtrate is chromatographed on a column of 150 g of silica gel. 7β-(D-5-Diphenylmethoxycarbonyl-5-phthalimidon-valeroylamino)-ceph-3-em-4-carboxylic acid diphenylmethyl ester which is pure according to a thin layer chromatogram is eluted with methylene chloride containing 3—4% of methyl acetate and is lyophilised from dioxane; thin layer chromatogram (silica gel plates; detection with iodine vapour): Rf=0.62 (system: toluene/acetone, 4:1); Rf=0.80 (system: toluene/acetone, 2:1) and Rf=0.79 (system: toluene/ethyl acetate, 2:1).

The starting material can be manufactured as follows:

A suspension of 20.0 g of 3-acetoxymethyl-7β-(D-5carboxy-5-phthalimido-n-valeroyl-amino)-ceph-3-em-4carboxylic acid in 400 ml of distilled water is treated with 71 ml of a 1 N aqueous sodium hydroxide solution. After addition of 0.4 g of the acetyl-esterase from Bacillus subtilis ATCC 6,633, the resulting solution is stirred for 20 hours at 37° C. whilst maintaining a constant pH-value of 7.3; the acetic acid liberated during the enzymatic saponification is neutralised with 32 ml of 1 N aqueous sodium hydroxide solution. After completion of the reaction, ethyl acetate is added followed, whilst cooling to 0° C. and stirring, by 20% strength aqueous phosphoric acid until a pH-value of 2.3 is reached. The aqueous phase is saturated with sodium chloride and re-extracted three more times with 300 ml of ethyl acetate. The organic extracts are washed with a saturated aqueous sodium chloride solution, dried with sodium sulphate and evaporated.

The crude 7β-(D-5-carboxy-5-phthalimido-n-valeroylamino)-3-hydroxymethyl-ceph-3-em-4-carboxylic acid thus obtained is taken up in 320 ml of dioxane and 80 ml of methanol, 18 g of diphenyldiazomethane are added in portions and the mixture is stirred for 3 hours at room temperature. The solution is evaporated to dryness and digested twice with 400 ml of diethyl ether. The residue is dissolved in benzene and chromatographed on 200 g of acid-washed silica gel; (column chromatography; column diameter: 4.15 cm); fractions of 100 ml each are withdrawn. The column is washed with 300 ml of benzene, 300 ml of a 9:1 mixture of benzene and ethyl acetate and 300 ml of a 5:5 mixture of benzene and ethyl acetate; these fractions are discarded. The next 400 ml of the 5:5 mixture of benzene and ethyl acetate serve to elute the 7β-(D-5-diphenyl-methoxycarbonyl-5-phthalimido-n-valeroylamino)-3-hydroxymethyl-ceph-3-em-4-carboxylic acid diphenylmethyl ester which after crystallisation from a mixture of ethyl acetate and cyclohexane melts at 113°–115° C.; $[\alpha]_D^{20} = +5°\pm 1°$ (c=1.131 in chloroform); ultraviolet absorption spectrum (in 95% strength ethanol): $\lambda_{max}=259$ mμ (ε=9,100) and $\lambda_{infl.}=241$ mμ (ε=14,600); thin layer chromatogram (silica gel; development with iodine): Rf=0.11 (system: toluene/acetone, 4:1).

A solution of 0.77 g of 7β-(D-5-diphenylmethoxycarbonyl-5-phthalimido-n-valeroyl-amino)-ceph-3-em-4carboxylic acid diphenylmethyl ester in 15 ml of absolute dimethylsulphoxide and 15 ml of acetic anhydride is left to stand for 6 hours in the dark at room temperature. The brownish-yellow reaction mixture is evaporated to dryness in a high vacuum, whilst adding absolute toluene. The residue is chromatographically purified on a 50-fold amount of silica gel. The amorphous 7β-(5-D-diphenylmethoxycarbonyl-5-phthalimido-n-valeroyl-amino)-3-formyl-ceph-3-em-4-carboxylic acid diphenylmethyl ester which is pure according to a thin layer chromatogram is eluted with methylene chloride containing 2–3% of methyl acetate; the fractions which consist of a single substance are combined, lyophilised from dioxane and dried in a high vacuum: infra-red absorption spectrum (in methylene chloride): characteristic bands at 2.90μ, 5.55μ, 5.62μ, 5.74μ, 5.81μ, 5.89μ, 5.93μ, 6.23μ, 6.68μ, 7.20μ, 8.16μ, 8.47μ and 9.15μ; thin layer chromatogram (silica gel; detection with iodine vapour or ultraviolet light, λ 254 mμ): Rf=0.63 (system: toluene/acetone, 4:1); Rf=0.84 (system: toluene/acetone, 2:1) and Rf=0.82 (system: toluene/ethyl acetate, 1:1).

EXAMPLE 4:

A solution of 1.25 g of crude crystals of 3-formyl-7β-[N-tert.-butoxycarbonyl-D-(α)-phenylglycyl]-amino-ceph3-em-4-carboxylic acid diphenylmethyl ester in 250 ml of degassed absolute benzene is treated with 1.86 g of tristriphenylphosphine-rhodium-I chloride. The reaction solution is warmed under an atmosphere of argon for 2 hours to 70° C. and for 5½ hours to the reflux temperature. After about 30 minutes, a finely crystalline precipitate separates out, and this redissolves over the course of about 3 hours. After completion of the reaction, the mixture is flushed with carbon monoxide for 10–15 minutes and is evaporated to dryness. The residue is taken up in a little methylene chloride and the solution is left to stand for one hour at about 4° C. The lemon-yellow crystalline bis-triphenylphosphinecarbonyl-rhodium-I chloride is filtered off, washed with cold methylene chloride and dried. The filtrate and the wash solutions are evaporated and purified by column chromatography on silica gel (addition of 10% of water). The chromatographically pure 7β-[N-tert.-butoxycarbonyl-D-(α)phenylglycyl]-amino-ceph-3-em-4-carboxylic acid diphenylmethyl ester is eluted with pure methylene chloride; detection on silica gel plates, systems: toluene/acetone, 4:1, and toluene/ethyl acetate, 2:1. The product crystallises from a mixture of methylene chloride, diethyl ether and cyclohexane in the form of colourless needles and melts at 126°–128° C. (uncorrected); a clear melt is observed at 145° C.; $[\alpha]_D^{20} = =40°\pm 1°$ (c=1.081 in chloroform); thin layer chromatogram (silica gel plates; identification with iodine vapour): Rf=0.39 (system: toluene/acetone, 19:1), Rf=0.56 (system: toluene/acetone, 14:1) and Rf=0.61 (system: toluene/ethyl acetate, 2:1); ultraviolet absorption spectrum (in 95% strength ethanol): $\lambda_{max}$ 255 mμ (ε=5,750) and $\lambda_{min}=238$ mμ (ε=4,950); infra-red absorption spectrum: characteristic bands at 2.89μ, 2.97μ, 5.62μ, 5.77μ, 5.83μ, 5.89μ, 6.11μ, 6.45μ, 6.69μ, 7.30μ, 7.72μ, 8.18μ, 8.56μ, 9.52μ, 9.71μ, 10.36μ, 13.19μ, 13.71μ and 14.36μ (in mineral oil) and at 2.70μ, 2.91μ, 5.58μ, 5.78μ, 5.82μ (shoulder), 5.88μ, 6.09μ, 6.61μ (shoulder) and 6.69μ.

The starting material can be manufactured as follows:

A suspension of 4.0 g of 3-acetoxymethyl-7β-[N-tert.-butoxycarbonyl-D-(α)-phenylglycyl]-amino-ceph-3-em-4carboxylic acid in 50 ml of water is treated wtih 7.7 ml of a 1 N aqueous sodium hydroxide solution. The clear solution is treated with 0.1 g of purified esterase from Bact. subtilis, strain ATCC 6,633 (compare British Pat. No. 1,080,904). The reaction solution is stirred at 35° C. and its pH-value is kept at 7.3 by adding 0.5 N aqueous sodium hydroxide solution; after consumption of 14.4 ml of the 0.5 N aqueous sodium hydroxide solution, the reaction is complete, (about 5 hours). The reaction solution is adjusted to pH 6.5 with 5 molar aqueous phosphoric acid, clarified with active charcoal, then covered with about 120 ml of ethyl acetate and acidified to pH 2.2 with 5-molar aqueous phosphoric acid whilst stirring. The solution, cooled with ice, is saturated with sodium chloride and the phases are separated; the aqueous layer is twice re-extracted with 100 ml of ethyl acetate at a time and is discarded. The organic extracts are washed four times with 30 ml at a time of a saturated aqueous sodium chloride solution and are briefly dried over anhydrous magnesium sulphate.

After filtration, the solution of the 3-hydroxymethyl-7β-[N-tert.-butoxycarbonyl-D-(α)-phenylglycyl]-amino-ceph-3-em-4-carboxylic acid, thus obtained, is treated with an excess of diphenyldiazomethane in cyclohexane and is left to stand for 45 minutes at room temperature. The solution, which is still slightly reddish in colour, is concentrated to a volume of about 200 ml, diethyl ether is added and the mixture is left to stand for 16 hours at about 4° C. The colourless crystals which hereupon precipitate are filtered off, washed with cold diethyl ether and dried in a vacuum desiccator. The crystalline 3-hydroxymethyl-7β[N-tert.-butoxycarbonyl-D-(α)-phenylglycyl]-amino-ceph-3-em-4-carboxylic acid diphenylmethyl ester thus obtainable decomposes at 128° C. The evaporated mother liquor contains a further quantity of the product, which can be isolated by column chromatography on silica gel.

100 g of benzoic anhydride are added to a solution of 11.5 g of 3-hydroxymethyl-7β-(N-tert.-butoxycarbonyl-D-αphenylglycyl)-amino-ceph-3-em-4-carboxylic acid diphenylmethyl ester in 150 ml of dimethylsulphoxide and the mixture is left to stand for 5 hours at 20° C. in the dark. The reaction mixture, which is orange-brown in colour, is washed three times with 1,500 ml of petroleum ether at a time (the petroleum ether solution is discarded), and the dimethylsulphoxide solution is poured, whilst stirring, into a mixture of 1,000 ml of diethyl ether, 500 ml of a 10% strength aqueous dipotassium hydrogen phosphate solution and about 300 g of ice. After stirring well, the aqueous phase is separated off and twice re-extracted with 500 ml of diethyl ether at a time. The combined organic extracts are successively washed with two portions, each of 500 ml, of a 5% strength aqueous dipotassium hydrogen phosphate solution, with 500 ml of water and twice with 500 ml at a time of a saturated aqueous sodium chloride solution, and are dried over magnesium sulphate and evaporated under reduced pressure. The oily residue is digested three times with 500 ml of petroleum ether at a time. The petroleum ether phase is discarded; the residue is dissolved in about 60 ml of diethyl ether and is stored for 16 hours at 0° C. The slightly beigecoloured crystals are filtered off, washed with a cooled mixture of diethyl ether and pentane and dried. The crude crystals thus obtainable, melting point 177°–178° C. (decomposition; uncorrected) contain 3-formyl-7β-(N-tert.-butoxycarbonyl-D-α-phenylglycyl)-amino-ceph-3-em-4-carboxylic acid diphenylmethyl ester and are used, without further purification, as the starting material.

The mother liquors contain a further quantity of the desired 3-formyl-7β(N-tert.-butoxycarbonyl-D-α-phenylglycyl)-amino-ceph-3-em-4-carboxylic acid diphenylmethyl ester and are purified by column chromatography on an approximately 40-fold amount of silica gel (with addition of 10% of water); the product is eluted with 8:2 and 9:1 mixtures of methylene chloride and toluene. The analytical preparation is crystallised from a mixture of methylene chloride, diethyl ether and cyclohexane and is dried for 18 hours in a high vacuum at 35° C.; the colourless crystals melt, with decomposition, at 181.5°–183° C. (uncorrected); $[\alpha]_D^{20} = -175° \pm 1°$ (c=1.029% in chloroform); thin layer chromatography (silica gel; detection with iodine vapour): Rf=0.66 (system: toluene/ethyl acetate, 2:1); ultraviolet absorption spectrum (in methylene chloride); $\lambda_{max} = 292$ mµ ($\epsilon = 13,900$) and $\lambda_{min} = 242$ mµ ($\epsilon = 3,500$); infrared absorption spectrum: characteristic bands at 2.92µ, 5.54µ, 5.78µ, 5.88µ, 5.97µ, 6.22µ, 6.68µ, 7.28µ, 8.15µ, 8.59µ, 9.14µ, 9.49µ, 9.98µ and 14.58µ (in methylene chloride) and at 2.98µ, 3.02µ, 5.56µ, 5.83µ, 5.92µ, 5.98µ, 6.28µ, 6.55µ, 7.98µ, 8.50µ, 9.14µ and 9.44µ.

Example 5

A solution of 0.566 g of 7β-phenylacetylamino-ceph-3-em-4-carboxylic acid diphenylmethyl ester in 2.5 ml of anisole and 10 ml of trifluoroacetic acid is left to stand for 20 minutes at room temperature and is then repeatedly evaporated to dryness, whilst adding toluene, until the trifluoroacetic acid has been completely removed. The residue is taken up in ethyl acetate and 0.5 molar aqueous dipotassium hydrogen phosphate solution and the phases are separated. The aqueous phase is twice washed with ethyl acetate and the organic solution is twice washed with 0.5 molar aqueous dipotassium hydrogen phosphate solution. The combined aqueous solutions are covered with fresh ethyl acetate and acidified with 20% strength aqueous phosphoric acid. The mixture is extracted with ethyl acetate and the organic solution is washed with a saturated aqueous sodium chloride solution, dried over magnesium sulphate and evaporated to dryness under reduced pressure. The residue is chromatographed on a 50-fold amount of silica gel (washed with concentrated hydrochloric acid) and the 7β-phenylacetylamino-ceph-3-em-4-carboxylic acid is eluted with methylene chloride containing 10–20% of methyl acetate. The fractions which according to a thin layer chromatogram are a single substance are crystallised from a mixture of methyl acetate and cyclohexane; the colourless crystals melt at 190°–191° C.; thin layer chromatogram (silica gel; development with iodine vapour or identification under ultraviolet light); Rf=0.58 (system: n-butanol/acetic acid/water, 75:7.5:21), Rf=0.265 (system: n-butanol/ethanol/water, 40:10:50), Rf=0.53 (system: n-butanol/acetic acid/water, 40:10:40), Rf=0.43 (system: ethyl acetate/pyridine/acetic acid/water, 62:21:6:11) and Rf=0.43 (system: ethyl acetate/n-butanol/pyridine/acetic acid/water, 42:21:21:6:10).

Example 6

A solution of 0.485 g of 7β-phenylacetylamino-ceph-2-em-4α-carboxylic acid diphenylmethyl ester in 15 ml of absolute methylene chloride is cooled to 0° C. in an ice bath and 0.190 g of purified 3-chloro-perbenzoic acid is added. The clear solution is left to stand for one hour at room temperature, diluted with 10 ml of methylene chloride and successively extracted with two 10 ml portions of each of: a 5% stength aqueous sodium bisulphite solution, an 0.5-molar aqueous dipotassium hydrogen phosphate buffer and distilled water; the aqueous phases are re-extracted with a little methylene chloride and discarded. The organic extracts are dried over magnesium sulphate and concentrated to a small volume. After adding diethyl ether and a little cyclohexane whilst warm, the 1-oxide of 7β-phenylacetylamino-ceph-3-em-4-carboxylic acid diphenylmethyl ester separates out as a voluminous, colourless crystalline product, melting point 192°–200° C. (decomposition). Both the crystalline product and the mother liquors still contain, according to a thin layer chromatogram (silica gel plates; system, toluene/acetone, 4:1), a small amount of starting material.

The product is chromatographed on 25 g of silica gel. A small amount of unchanged starting material is isolated with a 4:1 mixture of methylene chloride and methyl acetate, whilst with 9:1 and 6:1 mixtures of methylene chloride and methyl acetate the 1-oxide of 7β-phenylacetylamino-ceph-3-em-carboxylic acid diphenylmethyl ester is eluted. The product crystallises from a mixture of methylene chloride and diethyl ether in the form of spherical aggregates which after drying in a high vacuum at 35° C. for 17 hours melt with decomposition at 198°–202° C. (uncorrected); $[\alpha]_D^{20} = +112° \pm 1°$ (c=0.667 in chloroform); thin layer chromatogram (silica gel; development with iodine vapour): Rf=0.08 (system: toluene/ethyl acetate, 2:1), Rf=0.17 (system: toluene/ethyl acetate, 1:1), Rf=0.20 (system: toluene/acetone, 4:1) and Rf=0.57 (system: methylene chloride/acetone, 6:1); ultraviolet absorption (95% strength aqueous ethanol): $\lambda_{max} = 264$ mµ ($\epsilon = 6,860$) and $\lambda_{min} = 240$ mµ ($\epsilon = 3,930$); infra-red absorption spectrum: characteristic bands at 2.93µ, 5.54µ, 5.77µ, 5.92µ, 6.09µ, 6.68µ, 7.15µ, 8.13µ, 8.69µ, 9.10µ, 9.62µ, 9.84µ, 10.18µ and 10.23µ (in methylene chloride) and at 3.02µ, 5.53µ, 5.83µ, 6.06µ, 6.11µ, 6.52µ, 7.13µ, 7.76µ, 7.88µ, 8.57µ, 9.69µ and 10.44µ (in mineral oil).

Example 7

A solution of 0.50 g of the 1-oxide of 7β-phenylacetylamino-ceph-3-em-4-carboxylic acid diphenylmethyl ester in 10 ml of degassed dimethylformamide is cooled to about −30° C. under nitrogen, 0.7 ml (1.1 g) of phosphorus trichloride is then added and the mixture is stirred for 20 minutes at −20° C. to −25° C. The reaction solution is diluted with 30 ml of methylene chloride and is stirred with 50 ml of ice-cooled 1-molar aqueous dipotassium hydrogen phosphate solution. The aqueous phase is separated off and re-extracted with 30 ml of methylene chloride. The combined organic extracts are twice washed with 30 ml of water at a time, dried over magnesium sulphate and evaporated under reduced pressure. The oily residue, which contains dimethylformamide, is treated, whilst warm, with about 40 ml of diethyl ether and with a little cyclohexane, whereupon fine felted needles form. The mixture is left to stand at 4° C. and the product is filtered off and washed with a mixture of diethyl ether and pentane. The 7β-phenylacetylamino-ceph-3-em-4-carboxylic acid diphenylmethyl ester thus obtainable melts at 163°–164° C. (uncorrected).

Example 8

A solution of 0.50 g of amorphous 7β-phenylacetylamino-ceph-2-em-4α-carboxylic acid diphenylmethyl ester in 25 ml of absolute pyridine is left to stand for 17 hours in the dark under nitrogen. The pyridine is removed under reduced pressure and the residue is repeatedly treated with absolute toluene and again evaporated to dryness. The practically colourless, glassy residue which according to a thin layer chromatogram (silica gel; system toluene/ethyl acetate, 4:1 or toluene/acetone, 9:1) consists almost exclusively of 7β-phenylacetylamino-ceph-3-em-4-carboxylic acid diphenylmethyl ester, Rf-values 0.35 or 0.39, respectively, contains only traces of starting material, Rf=0.31 or 0.35, respectively, is dissolved in a little methylene chloride and treated with diethyl ether and cyclohexane whilst warm. The desired 7β-phenylacetylamino-ceph-3-em-4-carboxylic acid diphenylmethyl ester crystallises in the form of fine felted needles which melt at 162.5°–164° C. The analytical product is again crystallised from the same solvent mixture and is dried for 18 hours in a high vacuum at 35° C., melting point 163.5°–164.5° C. (uncorrected).

Example 9

A solution of 1.65 g of amorphous, almost colourless 7β-(D-5-diphenylmethoxycarbonyl-5-phthalimido-n-valeroylamino)-ceph-3-em-4-carboxylic acid diphenylmethyl ester in 100 ml of absolute methylene chloride is cooled to about −20° C. whilst flushing with nitrogen and is successively treated with 1.93 ml of absolute pyridine and 15.8 ml of an 8% strength solution of phosphorus pentachloride in absolute methylene chloride. After standing for one hour at −5° to −10° C., the solution which is a pale yellow-brown in colour, is cooled to below −20° C. and 13.4 ml of absolute methanol are added with good stirring in such a way that the internal temperature does not rise above −10° C. The mixture is left to react for 1 hour at this temperature and for 1 hour at room temperature before adding about 20 ml of a 1-molar aqueous potassium hydrogen phosphate solution with vigorous stirring. 5-molar aqueous phosphoric acid is added dropwise to the two-phase mixture until a pH-value of 2.0 is reached. After stirring well for 20 minutes at room temperature, the phases are separated; the aqueous phase is twice re-extracted with 35 ml of methylene chloride at a time, and is discarded. The combined organic extracts are washed with distilled water, dried over magnesium sulphate and freed of the solvent under reduced pressure. The oily residue is chromatographed on 100 g of silica gel (with addition of 5% of water). The colourless 7β-amino-ceph-3-em-4-carboxylic acid diphenylmethyl ester is eluted with methylene chloride containing 2–3% of methyl acetate and is crystallised from a mixture of methylene chloride and diethyl ether, melting point 152.5°–154° C. (uncorrected); $[\alpha]_D^{20} = +53° \pm 1°$ (c=0.981 in chloroform): ultraviolet absorption spectrum (in 95% strength ethanol): $\lambda_{max}$=255 mμ (ε=5,500) and $\lambda_{min}$=236 mμ (ε=4,650); infra-red absorption spectrum (in methylene chloride): characteristic bands at 2.91μ, 5.61μ, 5.78μ, 6.11μ, 7.14μ, 8.15μ, 8.29μ, 9.14μ and 9.83μ.

Example 10

A solution of 19.50 g of 7β-[N-tert.-butoxycarbonyl-D-(α)-phenylglycyl]-amino-ceph-3-em-4-carboxylic acid diphenylmethyl ester in a mixture of 200 ml of trifluoroacetic acid and 40 ml of anisole is left to stand for 10 minutes at 20° C. After adding 200 ml of absolute toluene, the reaction mixture is evaporated to dryness under reduced pressure. The residue is digested with about 300 ml of diethyl ether and the mixture is filtered. The colourless pulverulent precipitate is thoroughly washed with diethyl ether and dried in a waterpump vacuum; the salt of 7β-[D-(α)-phenylglycyl]-amino-ceph-3-em-4-carboxylic acid with trifluoroacetic acid is thus obtained.

The above product is dissolved in 70 ml of a 6:3:1 mixture of methanol, diethyl ether and water and a 50% strength solution (v/v) of triethylamine in the same solvent mixture is added, whilst cooling to 0° C.–5° C., until a pH-value of 4.5 is reached. The suspension which hereupon results is filtered at 0°–5° C. after 2 hours. The fine white precipitate is washed with a little ice-cooled solvent mixture of the above composition and is thoroughly washed with methylene chloride and diethyl ether and dried. After additional drying for 16 hours in a high vacuum at room temperature and over phosphorus pentoxide, 7β-[D-(α)-phenylglycyl]-amino-ceph-3-em-4-carboxylic acid is obtained in the form of the zwitter-ion, melting point 178°–179.5° C. (decomposition; uncorrected); $[\alpha]_D^{20} = +116° \pm 1°$ (c=0.864 in 0.1 N aqueous sodium bicarbonate solution); thin layer chromatogram (silica gel; detection with ultraviolet light, λ 254μ or ninhydrin): Rf=0.30 (system: n-butanol/acetic acid/water, 67:10:23), Rf=0.61 (system: isopropanol/formic acid/water, 77:4:19) and Rf=0.13 (system: ethyl acetate/n-butanol/pyridine/acetic acid/water, 42:21:21:6:10); ultraviolet absorption spectrum (in water): $\lambda_{max}$=253 mμ (ε=4,950) and $\lambda_{min}$=277 mμ (ε=4,550); infra-red absorption spectrum (in mineral oil): characteristic bands at 2,83μ, 3.10μ, 3.25μ (shoulder), 3.78μ, 5.59μ, 5,90μ, 6.10μ (shoulder), 6.38μ, 7.05μ, 7.35μ, 7.77μ, 7.98μ, 8.32μ, 8.50μ, 8.82μ, 10.08μ, 12.15μ, 13.20μ, 13.66μ, 13.90μ and 14.33μ.

The mother liquors are treated with about 20 ml of ethanol and left to stand for 16 hours at 0°–5° C. The pale beige-coloured crystals are filtered off, washed with cold ethanol and with diethyl ether and dried in a waterpump vacuum; the pale-coloured second batch of crystals is identical, according to thin layer chromatography, with the above product.

Example 11

The following compounds can be obtained analogously on choosing the suitable starting substances and, if necessary, after additional conversion:
7β-Phenylacetylamino-ceph-3-em-4-carboxylic acid [di-(4-methoxyphenyl)-methyl] ester;

7β-phenylacetylamino-ceph-3-em-4-carboxylic acid benzyl ester;

7β-phenyloxyacetylamino-ceph-3-em-4-carboxylic acid, thin layer chromatogram (silica gel): Rf=0.4 –0.5 (system: n-butanol/acetic acid/water, 75:7.5:21);

7β-(β-thienylacetyl-amino)-ceph-3-em-4-carboxylic acid, thin layer chromatogram (silica gel): Rf=0.5–0.6 (system: n-butanol/pyridine/acetic acid/water, 38:24:8:30); ultraviolet absorption spectrum (in 0.1-molar aqueous sodium bicarbonate solution): $\lambda_{max}$ at 237 mμ; infra-red absorption spectrum (in mineral oil): characteristic band at 5.62μ;

7β-(1-Tetrazolylacetyl-amino)-ceph-3-em-4-carboxylic acid, thin layer chromatogram (silica gel): Rf=0.4–0.5 (system: n-butanol/pyridine/acetic acid/water, 42:24:4:30); ultraviolet absorption spectrum (in methanol): $\lambda_{max}$ at 255 mμ;

7β-(1-methyl-2-imidazolylthio-acetyl)-amino-ceph-3-em-4-carboxylic acid, thin layer chromatogram (silica gel): Rf=0.3–0.4 (system: n-butanol/pyridine/acetic acid/water, 42:24:4:30); ultraviolet absorption spectrum (in methanol): $\lambda_{max}$ at 252 mμ;

7β-(α-phenyl-α-2,2,2-trichloroethoxycarbonyloxy-acetylamino)-ceph-3-em-4-carboxylic acid diphenylmethyl ester;

7β-(α-hydroxy-α-phenylacetyl-amino)-ceph-3-em-4-carboxylic acid;

7β-(4-pyridylthioacetyl-amino)-ceph-3-em-4-carboxylic acid amorphous; thin layer chromatogram (silica gel): Rf=0.35–0.45 (system: n-butanol/pyridine/acetic acid/water 42:24:4:30); infra-red absorption spectrum (in mineral oil): characteristic band at 5.62μ;

7β-acetoacetyl-amino-ceph-3-em-4-carboxylic acid, thin layer chromatogram (silica gel); Rf=0.3–0.4 (system: n-butanol/acetic acid/water 75:7.5:21); ultraviolet absorption spectrum (in 0.1 M aqueous sodium bicarbonate solution): $\lambda_{max}$ at 238 mμ and 265 mμ;

7β-cyanoacetylamino-ceph-3-em-4-carboxylic acid, thin layer chromatogram (silica gel); Rf=0.45–0.55 (system: n-butanol/pyridine/acetic acid/water 38:24:8:30); ultraviolet absorption spectrum (in 0.1-molar aqueous sodium bicarbonate solution): $\lambda_{max}$ at 254 mμ; infra-red absorption spectrum (in mineral oil): characteristic bands at 4.32μ and 5.60μ;

7β-α-cyanopropionyl-amino-ceph-3-em-4-carboxylic acid, thin layer chromatogram (silica gel): Rf=0.5–0.6 (system: n-butanol/pyridine/acetic acid/water 38:24:8:30); ultraviolet absorption spectrum (in 0.1-molar aqueous sodium bicarbonate solution): $\lambda_{max}$ at 255 mμ; infra-red absorption spectrum (in mineral oil): characteristic bands at 4.44μ and 5.62μ;

7β-(α-cyano-phenylacetyl)-amino-ceph-3-em-4-carboxylic acid, thin layer chromatogram (silica gel): Rf=0.3–0.4 (system: n-butanol/acetic acid/water 75:7.5:21); ultraviolet absorption spectrum (in 0.1-molar aqueous sodium bicarbonate solution): $\lambda_{max}$ at 260 mμ; infra-red absorption spectrum (in mineral oil): characteristic bands at 4.42μ and 5.62μ;

7β-[α-(N-tert.-butoxycarbonyl-amino)-α-2-thienyl-acetyl]-amino-ceph-3-em-4-carboxylic acid, thin layer chromatogram (silica gel): Rf=0.5–0.6 (system: ethyl acetate/pyridine/acetic acid/water, 62:21:6:11);

7β-(α-amino-α-2-thienylacetyl)-amino-ceph-3-em-4-carboxylic acid as the zwitter ion, thin layer chromatogram (silica gel): Rf=0.4–0.5 (system: ethyl acetate/methyl ethyl ketone/formic acid/water, 50:30:10:10); and 7β-phenylacetylamino-ceph-3-em-4-carboxylic acid diphenylmethyl ester-1-oxide, melting point 198°–202° C. (uncorrected); $[\alpha]_D^{20} = +112° \pm 1°$ (c=0.667 in chloroform); ultraviolet absorption (95% strength aqueous ethanol); $\lambda_{max}=264$ mμ (ε=6,860) and $\lambda_{min}=240$ mμ (ε=3,930).

Example 12

A solution of 0.955 g of 7β-phenylacetyl-amino-ceph-3-em-4-carboxylic acid in 60 ml of absolute methylene chloride is treated with 0.720 g of trimethylchlorosilane and 0.474 g of absolute pyridine. The mixture is stirred for 60 minutes at room temperature and cooled to −20° C., and a solution of 3.20 g of absolute pyridine in 30 ml of absolute methylene chloride and 23.4 ml of an 8% strength solution of phosphorus pentachloride in absolute methylene chloride are then added successively. The whole is stirred for 60 minutes at −10° C. to −12° C. and again cooled to about −20° C., and 15 ml of absolute methanol are then run in. The mixture is stirred for 25 minutes at −10° C. and then for 35 minutes at room temperature, 15 ml of water are added, the pH-value of the reaction mixture is raised from 1.8 to 2.2 by dropwise addition of triethylamine and the mixture is stirred for 20 minutes at room temperature. The pH-value is raised to 3.8 by renewed addition of triethylamine and the two-phase mixture is stirred for 90 minutes whilst cooling in an ice bath and is then filtered. The filter residue is washed with methanol, methylene chloride and diethyl ether and is dried in a vacuum desiccator. 7β-Amino-ceph-3-em-4-carboxylic acid is thus obtained in the amorphous form; the product is used further without purification.

Example 13

A solution of 1.94 g of 7β-phenylacetylamino-ceph-3-em-4-carboxylic acid diphenylmethyl ester in 100 ml of absolute methylene chloride is cooled to −15° C., 3.86 ml of absolute pyridine and 31.6 ml of an 8% strength solution of phosphorus pentachloride in methylene chloride are then added and the reaction mixture is stirred for 30 minutes at −10° C. and for a further 30 minutes at −5° C. The golden yellow solution is cooled to −20° C. and 26.8 ml of absolute methenol are added at such speed that the internal temperature does not rise to above −10° C. The reaction mixture is stirred for one hour at −10° C., left to stand for a further hour at 25°–30° C., and then treated with 80 ml of an 0.5-molar aqueous potassium dihydrogen phosphate solution with vigorous stirring. The pH-value of the two-phase reaction mixture is adjusted to 2 by dropwise addition of 20% strength phosphoric acid, the mixture is stirred for 20 minutes at room temperature and the phases are separated. The aqueous solution is twice washed with methylene chloride; the combined organic solutions are washed with two portions each of 20 ml of water and are dried over anhydrous magnesium sulphate.

The solvent is removed under reduced pressure; the oily residue is applied to a column of 110 g of silica gel (5% water content). Phenylacetic acid methyl ester is eluted with methylene chloride and 7β-amino-ceph-3-em-4-carboxylic acid diphenylmethyl ester is eluted with methylene chloride containing 3% of methyl acetate and is crystallised by dissolving in a small amount of methylene chloride and treating the warm solution with diethyl ether (needle-shaped crystals); the crystals are washed with cold diethyl ether and dried, melting point 153°–154° C.; thin layer chromatogram (silica gel): Rf=0.50 (system: toluene/acetone, 4:1), Rf=0.65 (system: toluene/acetone, 2:1), Rf=0.40 (system: toluene/ethyl acetate, 1:1) and Rf=0.33 (system: toluene/diethyl ether, 1:1); ultraviolet absorption spectrum: $\lambda_{max}=257$ mμ ($\epsilon=8,150$) and $\lambda_{min}=245$ mμ ($\epsilon=7,730$) (in methylene chloride) and $\lambda_{max}=255$ mμ ($\epsilon=5,500$) and $\lambda_{min}=236$ mμ ($\epsilon=4,650$) (in 95% ethanol); infra-red absorption spectrum: characteristic bands at 2.91μ, 2.97μ, 5.61μ, 5.78μ, 6.11μ, 7.14μ, 8.15μ, 8.29μ, 9.14μ and 9.83μ (in methylene chloride) and at 2.99μ, 5.65μ, 5.77μ, 6.08μ, 7.14μ, 7.74μ, 7.84μ, 8.08μ, 8.53μ, 9.14μ, 9.85μ and 10.35μ (in mineral oil).

Example 14

0.380 g of 7β-amino-ceph-3-em-4-carboxylic acid diphenylmethyl ester is covered with 2 ml of anisole and 8 ml of absolute trifluoroacetic acid, and the clear solution is left to stand for 10 minutes at room temperature and is then diluted with about 20 ml of absolute toluene. The mixture is evaporated under reduced pressure; the residue is twice more evaporated to dryness with addition of toluene and is then suspended in 5 ml of methanol, 5 ml of diethyl ether and 0.5 ml of water. The pH-value of the suspension is adjusted to 3.5 by dropwise addition of a 5% strength solution of triethylamine in methanol the suspension is left to stand for 30 minutes in an ice bath and the fine precipitate is filtered off by means of a suitable sintered glass filter. The slightly beige-coloured filter residue is washed with a mixture of methanol and methylene chloride and then with diethyl ether and is dried under reduced pressure at 35° C. The 7β-amino-ceph-3-em-4-carboxylic acid thus obtainable as a fine microcrystalline powder decomposes at 215° C.; thin layer chromatogram (silica gel; development with iodine): Rf=0.12 (system: n-butanol/acetic acid/water, 67:10:23), Rf=0.28 (system: n-butanol/pyridine/acetic acid/water, 40:24:6:30) and Rf=0.21 (system: ethyl acetate/n-butanol/pyridine/acetic acid/water, 42:21:21:6:10); infra-red absorption spectrum (in mineral oil): characteristic bands at 3.12μ, 3.80μ, 4.12μ (shoulder), 4.92μ, 5.54μ, 6.05μ (shoulder), 6.19μ, 6.55μ, 7.05μ, 7.42μ, 8.23μ, 8.79μ, 9.55μ, 12.08μ, 12.69μ and 13.04μ.

EXAMPLE 15

The 7β-amino-ceph-3-em-4-carboxylic acid described in Example 12 can be N-acylated, and converted into 7-(N-Ac-amino)-ceph-3-em-4-carboxylic acids, in accordance with the following general processes:

Variant A:

0.4 mmol of an acid [AcOH] is dissolved in 4 ml of absolute methylene chloride with the addition of 0.056 ml (0.4 mmol) of triethylamine [stock solution: 28.0 ml (200 mmols) of triethylamine, diluted to 100 ml with methylene chloride]. 0.0452 ml (0.4 mmol) of trichloroacetic acid chloride in 0.2 ml of methylene chloride [stock solution 22.6 ml (200 mmols) of trichloroacetic acid chloride diluted to 100 ml with methylene chloride] is added to the former solution which has been cooled to −15° C., and the mixture is stirred for 30 minutes at −15° C. The solution with the mixed anhydride [Ac—O—C(=O)—CCl₃] is treated with a finely dispersed suspension, cooled to −15° C., of 0.040 g (0.2 mmol) of 7-amino-ceph-3-em-4-carboxylic acid and 0.056 ml (0.4 mmol) of triethylamine in 4 ml of methylene chloride and the mixture is vibrated for 30 minutes at −15° C. and then for 30 minutes at 20° C. in an ultrasonics bath. The usually brown reaction solution is evaporated to dryness under reduced pressure and the resulting residue is partitioned between 10 ml of a 10% strength aqueous dipotassium hydrogen phosphate solution (pH 8.9) and 5 ml of ethyl acetate. The aqueous phase is adjusted to pH 2.6 with 20% strength aqueous phosphoric acid and is thereafter exhaustively extracted with ethyl acetate. The ethyl acetate extract (30–50 ml) is washed with water and dried over sodium sulphate, and evaporated under reduced pressure. The residue, in a suitable solvent system, is preparatively chromatographed for 2–5 hours on silica gel on a thin layer plate. After drying the plate at room temperature in a nitrogen atmosphere, the silica gel zone which absorbs under ultraviolet light (254 mμ) is mechanically detached from the plate and extracted three times with 10 to 30 ml of ethanol or methanol. After evaporating the extract under reduced pressure, 7β-Ac-amino-ceph-3-em-4-carboxylic acid is obtained as a beige or almost colourless residue.

If the thin layer plate possesses more than one zone which absorbs in ultraviolet light, the individual zones are separately worked-up as described above. A sample of the material resulting from the various zones is tested against Staphylococcus aureus in the plate diffusion test. The material from the micro-biologically most active zone is subjected to a renewed preparative thin layer separation, in which the product which chromatographically is a single substance can be isolated.

Variant B:

0.2 mmol of the sodium salt of an acid [AcONa] in 2 ml of absolute dimethylformamide is treated with 0.2 mmol of trichloroacetyl chloride as in Variant A, reacted with a solution of 0.2 mmol of 7β-amino-ceph-3-em-4-carboxylic acid and 0.2 mmol of triethylamine in 2 ml of dimethylformamide as in Variant A, and worked-up.

Variant C:

A mixture of 0.25 mmol of an acid chloride [AcCl] in 2 ml of methylene chloride is added to a solution, cooled to −15° C., of 0.040 g (0.2 mmol) of 7β-amino-ceph-3-em-4-carboxylic acid and 0.070 ml (0.5 mmol) of triethylamine in 5 ml of methylene chloride, and reacted and worked-up as in Variant A.

EXAMPLE 16

A suspension of 0.20 g of N-(2,2,2-trichloroethoxycarbonyl)-D-α-phenylglycine in 6 ml of a 1:1 mixture of tetrahydrofurane and acetonitrile is treated with 0.085 ml of triethylamine. After cooling to −10° C., 0.08 ml of chloroformic acid isobutyl ester is added dropwise with exclusion of moisture and the mixture is stirred for 15 minutes at −10° C. A solution consisting of 0.160 g of 7β-amino-ceph-3-em-4-carboxylic acid and 0.081 ml of triethylamine in 2 ml of a 1:1 mixture of water and tetrahydrofurane is added dropwise to the solution of the mixed anhydride in such a way that the internal temperature does not rise above 0° C. The reaction mixture is stirred for a further 30 minutes at 0° C. and then for 90 minutes at room temperature, and the bulk of the organic solvents is then evaporated under reduced pressure. The residue is diluted with 5 ml of an 0.5 molar aqueous dipotassium hydrogen phosphate solution and 5 ml of ethyl acetate. Undissolved material is filtered off by means of a sintered glass filter and a diatomaceous earth preparation. The layers of the filtrate are separated; the organic phase is re-extracted with the dipotassium hydrogen phosphate solution and discarded. The aqueous phases are washed with ethyl acetate, covered with fresh ethyl acetate and acidified to pH 2 with concentrated phosphoric acid. The organic phase is separated off and repeatedly washed with a saturated aqueous sodium chloride solution. The aqueous phases are twice re-extracted with 10 ml of ethyl acetate at a time, and discarded. The combined organic extracts are dried over sodium sulphate and freed of the solvent under reduced pressure. The crude product is chromatographed on 10 g of silica gel. Unchanged N-(2,2,2-trichloroethoxy-carbonyl)-D-α-phenylglycine is eluted with a 4:1 mixture of toluene/ethyl acetate. 7β-(N-2,2,2-Trichloroethoxycarbonyl-D-α-glycyl)-amino-ceph-3-em-4-carboxylic acid is eluted with the toluene-ethyl acetate mixture using increasing proportions of ethyl acetate relative to the 4:1 ratio. Infrared absorption spectrum (in mineral oil): characteristic bands at 5.61μ, 5.86μ, 5.92μ and 6.12μ; ultraviolet absorption spectrum (in ethanol): $\lambda_{max}$=252 mμ; thin layer chromatogram (silica gel; development with iodine vapour): Rf~0.8 (system: n-butanol/acetic acid/water, 71.5:7.5:21).

A solution of 0.120 g of 7β-(N-2,2,2-trichloroethoxycarbonyl-D-α-phenylglycyl)-amino-ceph-3-em-4-carboxylic acid in 6 ml of dimethylformamide is treated with 10 ml of 90% strength aqueous acetic acid and then with 0.600 g of zinc dust. The mixture is stirred for 1 hour at room temperature, the unreacted zinc dust is filtered off and rinsed with dimethylformamide, and the filtrate is stirred for about 10 minutes with 25 ml of an ion exchanger (Dowex 50-16; 20-50 mesh; sulphonic acid type, in the H-ion form). The exchanger is filtered off and washed with water. The filtrate is evaporated to dryness in a high vacuum at a bath temperature of below 30° C. (rotary evaporator). The residue is dissolved in 5 ml of an 8:2 mixture of methanol and water and adjusted to pH 4.3 with a 1% strength solution of triethylamine in methanol. The whole is stirred for 1 hour in an ice bath and evaporated to dryness, and the residue is digested with methylene chloride. The product is filtered off, thoroughly washed with methylene chloride and dried in a high vacuum. 7β-(D-α-Phenylglycyl-amino)-ceph-3-em-4-carboxylic acid, which is identical with the compound obtainable according to the process of Example 10, is thus obtained.

We claim:

1. A process for the manufacture of 7β-amino-ceph-em-4-carboxylic acid compounds of the formula

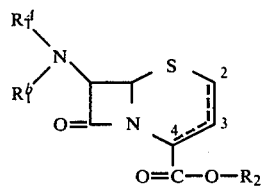

wherein $R_1{}^A$ is an acyl group of the formula

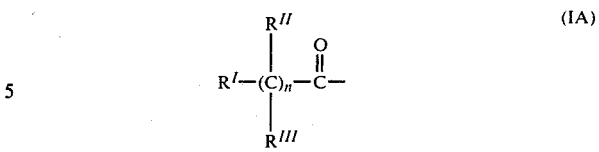

in which n represents O and $R^I$ represents cycloalkyl with 5-7 ring carbon atoms substituted by a member selected from the group consisting of amino and sulphoamino, or represents a member selected from the group consisting of phenyl, naphthyl and tetrahydronaphthyl, and these groups substituted by a member selected from the group consisting of hydroxyl, lower alkoxy and halogen, or represents 4-isoxazolyl and 4-isoxazolyl substituted by a member selected from the group consisting of lower alkyl, phenyl and halogenophenyl, or represents amino N-substituted by a member selected from the group consisting of lower alkyl and halogen-lower alkyl, or n represents 1, $R^I$ represents a member selected from the group consisting of lower alkyl and lower alkyl substituted by a member selected from the group consisting of halogeno, phenyloxy, hydroxy-phenyloxy, halogeno-phenyloxy, amino and carboxyl, or represents lower alkenyl or represents a member selected from the group consisting of phenyl, hydroxyl-phenyl, halogeno-phenyl and phenyloxy-phenyl, or represents a member selected from the group consisting of pyridyl, pyridinium, thienyl, 1-imidazolyl and 1-tetrazolyl or such heterocyclic radical substituted by a member selected from the group consisting of lower alkyl, amino and amino-methyl, or represents a member selected from the group consisting of lower alkoxy, phenyloxy, hydroxyl-phenyloxy and halogeno-phenyloxy, or represents a member selected from the group consisting of lower alkylthio and lower alkenylthio, or represents a member selected from the group consisting of phenylthio, 2-imidazolylthio, 1,2,4-triazol-3-ylthio, 1,3,4-triazol-2-ylthio, 1,2,4-thiadiazol-3-ylthio, 1,3,4-thiadiazol-2-ylthio and 5-tetrazolylthio, and such groups substituted by lower alkyl, or represents a member selected from the group consisting of halogeno, carboxyl, lower alkoxy-carbonyl, cyano, carbamoyl and carbamoyl N-substituted by a member selected from the group consisting of lower alkyl and phenyl, or represents a member selected from the group consisting of lower alkanoyl and azido, and $R^{II}$ and $R^{III}$ represent hydrogen, or n represents 1, $R^I$ represents a member selected from the group consisting of phenyl and thienyl and these groups substituted by a member selected from the group consisting of hydroxyl and halogeno, or represents 1,4-cyclohexadienyl, $R^{II}$ represents a member selected from the group consisting of amino, lower alkoxycarbonylamino, 2-halogeno-lower alkoxycarbonylamino, carbamoylamino, guanidinocarbonylamino, sulphoamino, azido, carboxyl, lower alkoxycarbonyl, cyano, sulpho, hydroxyl, lower alkoxycarbonyloxy, 2-halogeno-lower alkoxycarbonyloxy, lower alkoxy, phenyloxy and halogeno, and $R^{III}$ represents hydrogen, or n represents 1, $R^I$ and $R^{II}$ each represent a member selected from the group consisting of halogeno and lower alkoxycarbonyl, and $R^{III}$ represents hydrogen, or n represents 1 and each of the groups $R^I$, $R^{II}$ and $R^{III}$ represents lower alkyl, $R_1{}^b$ is hydrogen, and $R_2$ is a member selected from the group consisting of hydrogen, 2-halogeno-lower alkyl, phenacyl, nitrophenyl, polyhalogeno-phenyl, lower alkoxy-benzyl, nitro-benzyl, tert.-butyl, diphenylmethyl, 4,4'-dimethoxydiphenyl, bis-(4-methoxyphenyloxy)-methyl, trityl, lower alkanoylaminomethyl, carbamoylaminomethyl, ureidocarbonylaminomethyl quanidinocarbonylaminomethyl, or lower alkanoyloxymethyl, tri-lower alkyl-silyl and tri-lower alkyl-stannyl, and which cephem compounds contain a double bond in one of the positions 2,3 and 3,4, as well as 1-oxides of the formula I, in which the ring double bond is in the 3,4-position, or metal or ammonium salts of compounds of the formula I in which $R_2$ represents hydrogen, or acid addition salts of such compounds, wherein $R_1{}^a$ and $R_1{}^b$ represent hydrogen or which possess a basic group in the radical $R_1{}^a$ and $R_1{}^b$, or internal salts of such compounds which possess both types of salt-forming groups, characterized in that a 3-formylcephem-4-carboxylic acid compound of the formula

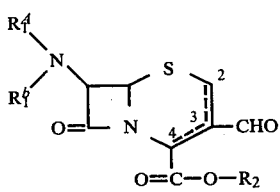
(II)

which contains a double bond in the 2,3-position, or a 1-oxide of a ceph-3-em compound of the formula II, is decarbonylated in the 3-position by treating in an inert solvent and at a temperature of between 10° C. to 150° C. with tris-triphenylphosphine-rodium-I-chloride, bis-triphenylphosphine-platinum-II-chloride, bis-triphenylphosphine-carbonyliridium-II-chloride or tris-triphenylphosphine-iridium-I-chloride.

2. Process according to claim 1, wherein tris-triphenylphosphine-rhodium-I-chloride is used as platinum metal complex.

3. Process according to claim 1, wherein the decarbonylation is carried out at about 40° C. to about 120° C.

4. The process of claim 1 in which a compound of the formula II, wherein $R_1{}^a$ is phenylacetyl, $R_1{}^b$ is hydrogen and $R_2$ is diphenylmethyl, is treated with tris-triphenylphosphine-rhodium-I-chloride.

5. The process of claim 1 in which a compound of the formula II, wherein $R_1{}^a$ is phenoxyacetyl, $R_1{}^b$ is hydrogen and $R_2$ is hydrogen, is treated with tris-triphenylphosphine-rhodium-I-chloride.

6. The process of claim 1 in which a compound of the formula II, wherein $R_1{}^a$ is D-5-diphenylmethoxycarbonyl-5-phthalimido-N-valeyl, $R_1{}^b$ is hydrogen and $R_2$ is diphenylmethyl, is treated with tris-triphenylphosphine-rhodium-I-chloride.

7. A process for preparing a compound of the formula

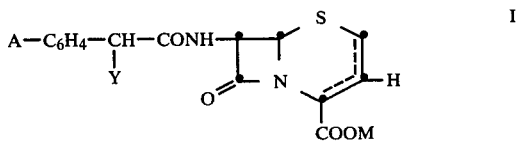
I wherein A is hydrogen, hydroxy and halogen; Y is $NH_2$; M is an easily removable protecting group; the broken line in the thiazine ring indicates a double bond at the 2,3 or 3,4-position comprising reacting a compound of the formula

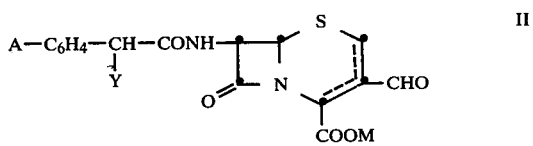
II wherein A, Y and M are as defined in formula I, the broken line in the thiazine ring indicates a double bond at the 2,3 or 3,4-position; with tris-(triphenylphosphine)-chlororodium, bis-triphenylphosphine-platinum-II-chloride, bis-triphenylphosphine-carbonyliridium-II-chloride or tris-triphenylphosphineridium-I-chloride in a compatible solvent at a temperature and for a length of time sufficient to cause decarbonylation without significant decomposition.

* * * * *